(12) United States Patent
Okuda et al.

(10) Patent No.: US 9,453,091 B2
(45) Date of Patent: Sep. 27, 2016

(54) METHOD OF PRODUCING WATER ABSORBENT RESIN

(75) Inventors: Sumio Okuda, Himeji (JP); Syuji Kanzaki, Himeji (JP); Kunihiko Ishizaki, Himeji (JP); Shinichi Fujino, Himeji (JP); Kozo Nogi, Himeji (JP)

(73) Assignee: Nippon Shokubai Co., Ltd., Osaka (JP)

( * ) Notice: Subject to any disclaimer, the term of this patent is extended or adjusted under 35 U.S.C. 154(b) by 267 days.

(21) Appl. No.: 13/635,045

(22) PCT Filed: Mar. 17, 2011

(86) PCT No.: PCT/JP2011/056423
§ 371 (c)(1),
(2), (4) Date: Nov. 26, 2012

(87) PCT Pub. No.: WO2011/115221
PCT Pub. Date: Sep. 22, 2011

(65) Prior Publication Data
US 2013/0123435 A1    May 16, 2013

(30) Foreign Application Priority Data
Mar. 17, 2010  (JP) .................... 2010-061223
Mar. 17, 2010  (JP) .................... 2010-061224

(51) Int. Cl.
| | |
|---|---|
| A61L 15/24 | (2006.01) |
| C08F 120/06 | (2006.01) |
| C08F 220/06 | (2006.01) |
| C08J 3/24 | (2006.01) |
| B07B 1/56 | (2006.01) |
| C08F 6/00 | (2006.01) |
| B07B 13/16 | (2006.01) |
| G01N 15/02 | (2006.01) |
| B07B 1/28 | (2006.01) |

(52) U.S. Cl.
CPC .............. *C08F 120/06* (2013.01); *B07B 1/56* (2013.01); *B07B 13/16* (2013.01); *C08F 6/008* (2013.01); *C08F 220/06* (2013.01); *C08J 3/24* (2013.01); *C08J 3/245* (2013.01); *G01N 15/0272* (2013.01); *B07B 1/28* (2013.01); *C08J 2300/14* (2013.01); *G01N 2015/0277* (2013.01); *G01N 2015/0288* (2013.01)

(58) Field of Classification Search
CPC ........... G01N 5/0272; G01N 2015/0277; G01N 2015/0288; B07B 1/28; B07B 1/56; B07B 1/54; C08J 3/24; C08F 220/06; C08F 120/06; C08F 6/008
USPC ............... 526/317.1; 209/3.1, 632, 659, 680
See application file for complete search history.

(56) References Cited

U.S. PATENT DOCUMENTS

| | | |
|---|---|---|
| RE32,649 E | 4/1988 | Brandt et al. |
| 5,149,335 A | 9/1992 | Kellenberger et al. |
| 5,562,646 A | 10/1996 | Goldman et al. |
| 6,164,455 A | 12/2000 | Kakita et al. |
| 6,414,214 B1 | 7/2002 | Engelhardt et al. |
| 6,716,894 B2 | 4/2004 | Kajikawa et al. |
| 6,727,345 B2 | 4/2004 | Kajikawa et al. |
| 6,849,665 B2 | 2/2005 | Frenz et al. |
| 7,169,843 B2 | 1/2007 | Smith et al. |
| 7,173,086 B2 | 2/2007 | Smith et al. |
| 7,193,006 B2 | 3/2007 | Ishizaki et al. |
| 2002/0128618 A1 | 9/2002 | Frenz et al. |
| 2005/0245684 A1 | 11/2005 | Daniel et al. |
| 2005/0256469 A1 | 11/2005 | Qin et al. |
| 2006/0102527 A1 | 5/2006 | Kato et al. |
| 2007/0293617 A1 | 12/2007 | Riegel et al. |
| 2008/0125533 A1 | 5/2008 | Riegel et al. |
| 2008/0202987 A1 | 8/2008 | Weismantel et al. |
| 2009/0194462 A1* | 8/2009 | Stueven et al. ............. 209/11 |
| 2010/0014612 A1 | 1/2010 | Wang et al. |
| 2010/0041550 A1 | 2/2010 | Riegel et al. |
| 2011/0003926 A1 | 1/2011 | Nogi et al. |
| 2011/0006140 A1 | 1/2011 | Ishizaki et al. |
| 2011/0009590 A1 | 1/2011 | Matsumoto et al. |
| 2011/0011491 A1 | 1/2011 | Matsumoto et al. |
| 2011/0015351 A1 | 1/2011 | Nogi et al. |
| 2011/0028670 A1 | 2/2011 | Matsumoto et al. |
| 2011/0088806 A1 | 4/2011 | Nogi et al. |
| 2011/0110730 A1 | 5/2011 | Nogi et al. |
| 2011/0166300 A1* | 7/2011 | Dairoku et al. .............. 525/384 |

FOREIGN PATENT DOCUMENTS

| | | |
|---|---|---|
| DE | 3520535 A1 | 12/1986 |
| DE | 3632069 A1 * | 3/1988 |
| JP | 54-45256 | 12/1979 |
| JP | 62034052 A * | 2/1987 |
| JP | 19-202187 | 4/1998 |
| JP | 11-116689 | 4/1999 |
| JP | 11-128844 | 5/1999 |
| JP | 11128844 A * | 5/1999 |
| JP | 11-156299 | 6/1999 |
| JP | 2004-294734 | 10/2004 |
| JP | A-2006-198576 | 8/2006 |

(Continued)

*Primary Examiner* — Karuna P Reddy
(74) *Attorney, Agent, or Firm* — Cesari and McKenna LLP

(57) ABSTRACT

A method for producing a water absorbent resin, the method including a polymerization step, a drying step, a classification step, and a surface crosslinking step. The classification step carried out before or after the surface crosslinking step requires use of a metal sieve mesh having stretch tension from 35 to 100 N/cm, in which an air jet cleaner or an air jet brush cleaner and plural tapping balls or tapping blocks are installed below the metal sieve mesh, a classification aid particle having specific gravity different from that of the water absorbent resin powder is added, and a fine powder of the water absorbent resin and the classification aid particle are removed.

7 Claims, 2 Drawing Sheets

(56) References Cited

FOREIGN PATENT DOCUMENTS

| JP | 2008-224261 | 9/2008 |
| JP | 2010-504417 | 6/2013 |
| WO | WO-A-2004/060584 | 7/2004 |
| WO | WO2006/074816 | 7/2006 |
| WO | WO2006/082189 | 8/2006 |
| WO | WO2006/082197 | 8/2006 |
| WO | WO 2009/113678 | 9/2007 |
| WO | WO2008/025652 | 3/2008 |
| WO | WO2008/025655 | 3/2008 |
| WO | WO2008/025656 | 3/2008 |
| WO | WO2008/092842 | 8/2008 |
| WO | WO2008/092843 | 8/2008 |
| WO | WO-2008123477 A1 | 10/2008 |
| WO | WO 2010032694 A1 * | 3/2010 |

* cited by examiner

# METHOD OF PRODUCING WATER ABSORBENT RESIN

CROSS REFERENCE TO RELATED APPLICATIONS

This application is a National Stage of International Application No. PCT/JP2011/056423 filed on Mar. 17, 2011, which claims priority to Japanese Application No. 2010-061224 filed Mar. 17, 2010 and Japanese Application No. 2010-061223 filed Mar. 17, 2010. The contents of the prior applications are incorporated herein by reference in their entirety.

TECHNICAL FIELD

The present invention relates to a method for producing a water absorbent resin, and more particularly, to a production method for obtaining a water absorbent resin exhibiting high liquid permeability under high pressure, by performing surface crosslinking.

BACKGROUND ART

A water absorbent resin (SAP/Super Absorbent Polymer) is a water-swellable and water-insoluble polymer gelling agent, and is frequently used primarily in disposable applications as water absorbent articles such as paper diapers and sanitary napkins, as well as water retention agents for agricultural and horticultural use, industrial water stopping materials and the like. As to such a water absorbent resin, many monomers and hydrophilic polymers have been proposed as raw materials. However, a polyacrylic acid (salt)-type water absorbent resin which uses acrylic acid and/or salts thereof as monomers is in particular industrially most frequently used due to their high water absorption performance.

The water absorbent resin is produced through various steps such as a polymerization step, a drying step, a pulverization step, a classification step, and a surface crosslinking step (Patent Literature 1 to 3). Furthermore, along with a performance improvement and thickness reduction of a paper diaper that is its principal application, there is a demand for an increase in use amount of water absorbent resin (for example, 50% by weight or more), and for many physical properties (functions). Examples thereof include absorption capacity, gel strength, extractables (Patent Literature 4), absorption speed, absorption capacity under load (Patent Literature 5), liquid permeability (Patent Literature 6 to 9), particle size distribution, urine resistance, antibacterial property, impact resistance, powder fluidity, deodorization property, coloration resistance, low dust property, and the like. Among these physical properties, liquid permeability is a more important factor, and there have been suggested many methods or technologies for improving liquid permeability under load such as SFC (Saline Flow Conductivity; Patent Literature 6) and GBP (Gel Bed Permeability; Patent Literature 7 to 9) and liquid permeability without load.

Furthermore, in connection with the physical properties described above, many technologies combining plural parameters have also been suggested. For example, a technology for defining impact resistance (FI) (Patent Literature 10), a technology for defining absorption speed (FSR/Vortex) or the like (Patent Literature 11), and a technology for defining the product of liquid diffusion performance and amount of core absorption after 60 minutes (DA60) (Patent Literature 12) are known.

Furthermore, as methods for enhancing liquid permeability (SFC, GBP or the like), there are known a technology of adding gypsum before polymerization or during polymerization (Patent Literature 13), a technology of adding a spacer (Patent Literature 14), a technology of using a nitrogen-containing polymer having a nitrogen atom of 5 to 17 [mol/kg] which is capable of protonation (Patent Literature 15), a technology of using a polyamine and a polyvalent metal ion or a polyvalent anion (Patent Literature 16), a technology of coating a water absorbent resin having pH of less than 6 with a polyamine (Patent Literature 17), and a technology of using polyammonium carbonate (Patent Literature 18).

In addition to these, a technology of using a polyamine at extractables portion of 3% by weight or more, and a technology of defining the suction index (WI) or gel strength (Patent Literature 19 to 21) are known. Furthermore, in order to improve coloration and liquid permeability, a technology of controlling methoxyphenol which is a polymerization inhibitor used at the time of polymerization and then using a polyvalent metal salt (Patent Literatures 22 and 23) is also known.

PRIOR LITERATURE

Patent Literature

Patent Literature 1: U.S. Pat. No. 6,727,345
Patent Literature 2: U.S. Pat. No. 7,193,006
Patent Literature 3: U.S. Pat. No. 6,716,894
Patent Literature 4: U.S. Reissue Pat. No. 32649
Patent Literature 5: U.S. Pat. No. 5,149,335
Patent Literature 6: U.S. Pat. No. 5,562,646
Patent Literature 7: US 2005/0256469
Patent Literature 8: U.S. Pat. No. 7,169,843
Patent Literature 9: U.S. Pat. No. 7,173,086
Patent Literature 10: U.S. Pat. No. 6,414,214
Patent Literature 11: U.S. Pat. No. 6,849,665
Patent Literature 12: US 2008/0125533
Patent Literature 13: US 2007/0293617
Patent Literature 14: US 2002/0128618
Patent Literature 15: US 2005/0245684
Patent Literature 16: WO 2006/082197 A
Patent Literature 17: WO 2006/074816 A
Patent Literature 18: WO 2006/082189 A
Patent Literature 19: WO 2008/025652 A
Patent Literature 20: WO 2008/025656 A
Patent Literature 21: WO 2008/025655 A
Patent Literature 22: WO 2008/092843 A
Patent Literature 23: WO 2008/092842 A

SUMMARY OF INVENTION

In the aforementioned Literature 1 to 23 etc., many surface crosslinking technologies, additives, and modifications of production processes have been suggested for an enhancement of the physical properties of water absorbent resins.

However, modification or addition of the raw materials of water absorbent resins, such as a surface crosslinking agent and additives (a polyamine polymer, an inorganic fine particle, a thermoplastic polymer and the like) have caused in some cases a decrease in the safety of the raw materials, an increase in cost, as well as a decrease in other physical properties. Furthermore, the addition of new production step not only causes high capital investment or an increase in cost due to the energy used therein, but also requires industrially complicated operation, so that the addition may rather cause a decrease in productivity or physical properties. Furthermore, there has also been a problem that in continuous production of a huge scale (particularly, 1 [t/hr] or more), physical property such as liquid permeability (SFC) deteriorates with the production time. Further, inspection of deterioration of the physical property takes time, so that a large amount of substandard products sometimes has been produced in the production of a huge scale.

Thus, in order to improve the problems described above, it is an object of the present invention to provide a method of enhancing and stabilizing the physical property (for example, liquid permeability) of a water absorbent resin by a simple technique, without requiring any modification of raw materials or high capital investment.

In order to solve the problems described above, the methods for producing a water absorbent resin of the present invention (first and second aspects of the invention) are as follows.

That is, a method for producing a water absorbent resin according to the present invention (first aspect of the invention) is a method for producing a water absorbent resin, which includes a polymerization step of polymerizing an aqueous solution of acrylic acid (salt) to obtain a water-containing gel-like crosslinked polymer; a drying step of drying the water-containing gel-like crosslinked polymer to obtain a water absorbent resin powder; a classification step of classifying the water absorbent resin powder; and a surface crosslinking step of surface crosslinking the water absorbent resin powder, wherein in the classification step that is carried out before the surface crosslinking step and/or after the surface crosslinking step, the stretch tension (tension) of a metal sieve mesh used in the classification step is from 35 [N/cm] to 100 [N/cm].

Furthermore, another method for producing a water absorbent resin according to the present invention (second aspect of the invention) is a method for producing a water absorbent resin, which includes a polymerization step of polymerizing an aqueous solution of acrylic acid (salt) to obtain a water-containing gel-like crosslinked polymer; a drying step of drying the water-containing gel-like crosslinked polymer to obtain a water absorbent resin powder; a classification step of classifying the water absorbent resin powder; and a surface crosslinking step of surface crosslinking the water absorbent resin powder, wherein in the classification step that is carried out before the surface crosslinking step and/or after the surface crosslinking step, an airbrush is used below the metal sieve mesh used in the classification step.

Meanwhile, the method for producing a water absorbent resin according to the present invention can also be referred to as a method for enhancing liquid permeability of a water absorbent resin. Furthermore, the method for producing a water absorbent resin according to the present invention can also be referred to as a method for classifying a water absorbent resin.

According to the present invention, in a method for producing a water absorbent resin including a polymerization step, a drying step, a classification step, and a surface crosslinking step, the physical property after surface crosslinking (for example, liquid permeability) can be enhanced, and deflection (standard deviation) of the physical property during continuous production or deterioration of the physical property resulting from continuous operation can be decreased.

EMBODIMENTS FOR CARRYING OUT THE INVENTION

Figure 1:
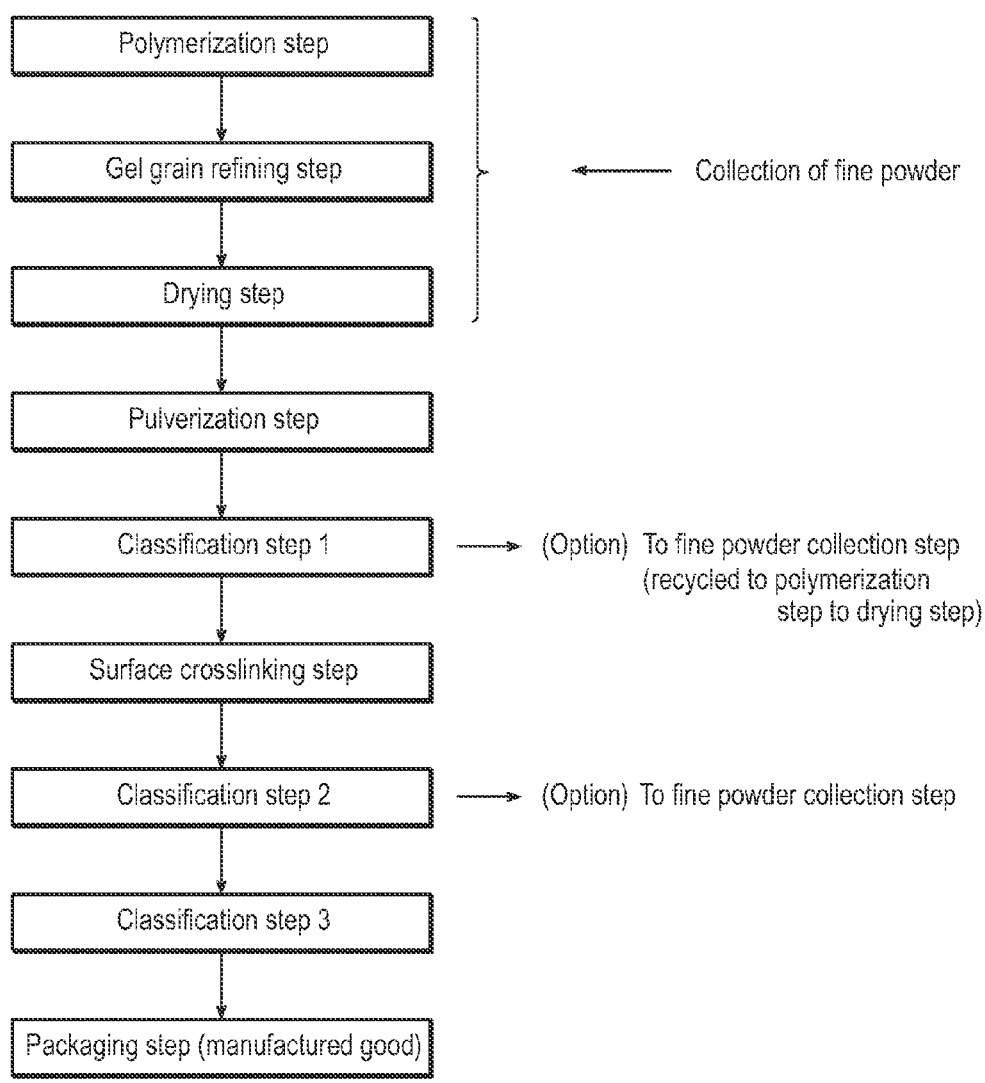
FIG. 1 is a representative flow diagram of a continuous process for a water absorbent resin.

Hereinafter, the method for producing a water absorbent resin according to the present invention will be described in detail. However, the scope of the present invention is not intended to be restrained by these descriptions, and embodiments other than the following examples can also be appropriately modified and carried out to the extent that the purport of the present invention is not impaired. Specifically, the present invention is not intended to be limited to the various exemplary embodiments described below, and can be modified into various embodiments within the scope illustrated by the claims. Exemplary embodiments that can be obtained by appropriately combining the technical means that are respectively disclosed in different exemplary embodiments, are also included in the technical scope of the present invention.

[1] DEFINITIONS OF TERMS (1-1) Water Absorbent Resin

The term "water absorbent resin" according to the present invention means a water-swellable and water-insoluble polymer gelling agent. Meanwhile, the term "water-swellable" means that the CRC (absorption capacity without load) defined in ERT441.2-02 is essentially 5 [g/g] or higher, preferably 10 to 100 [g/g], and still more preferably 20 to 80 [g/g]. The term "water-insoluble" means that the Ext (extractables) defined in ERT470.2-02 is essentially 0% to 50% by weight, preferably 0% to 30% by weight, more preferably 0% to 20% by weight, and particularly preferably 0% to 10% by weight.

The water absorbent resin can be appropriately designed in accordance with the application, and there are no particular limitations. However, the water absorbent resin is preferably a hydrophilic crosslinked polymer obtained by crosslink-polymerizing an unsaturated monomer having a carboxyl group. Furthermore, the water absorbent resin is not limited to the case in which the entire amount (100% by weight) is in the form of polymer, and the water absorbent resin may contain an additive and the like to the extent that the performance described above is maintained. That is, in the present invention, even a water absorbent resin composition is collectively referred to as a water absorbent resin. The content of a polyacrylic acid (salt)-type water absorbent resin is preferably 70% to 99.9% by weight, more preferably 80% to 99.7% by weight, and still more preferably 90% to 99.5% by weight, relative to the total amount. As another component other than the water absorbent resin, water is preferred from the viewpoints of absorption speed and impact resistance of the powder (particle), and optionally, an additive that is described below is included.

(1-2) Polyacrylic Acid (Salt)-Type Water Absorbent Resin

The term "polyacrylic acid (salt)-type water absorbent resin" according to the present invention refers to a water absorbent resin which composed principally of acrylic acid and/or a salt thereof (hereinafter, referred to as acrylic acid (salt)) as a repeating unit.

Specifically, it refers to a polymer which contains acrylic acid (salt) essentially 50% to 100% by mole, preferably 70% to 100% by mole, more preferably 90% to 100% by mole, and particularly preferably substantially 100% by mole, among all the monomers used in polymerization (excluding the crosslinking agent). The salt as a polymer essentially includes a water-soluble salt, and preferably includes a monovalent salt, still more preferably an acrylic metal salt or an ammonium salt, particularly an alkali metal salt, and further a sodium salt.

(1-3) EDANA and ERT

The term "EDANA" is an abbreviation for the European Disposables and Nonwovens Association, and the term "ERT" is an abbreviation for a method for analyzing a water absorbent resin (EDANA Recommended Test Method), which is a European standard (almost international standard).

Meanwhile, in the present invention, unless otherwise specified, the physical properties of a water absorbent resin or the like are measured according to the ERT original (published Literature: revised in 2002).

(a) CRC (ERT441.2-02)

The term "CRC" is an abbreviation for Centrifuge Retention Capacity, and means absorption capacity without load (hereinafter, also be referred to as "absorption capacity"). Specifically, the CRC is absorption capacity (unit: [g/g]) obtained after 0.200 g of a water absorbent resin in a non-woven fabric bag is allowed to freely swell for 30 minutes in a large excess of a 0.9 wt % aqueous solution of sodium chloride, and then is dehydrated in a centrifuge.

(b) "AAP" (ERT442.2-02)

The term "AAP" is an abbreviation for Absorption Against Pressure, and means absorption capacity under load. Specifically, the AAP is absorption capacity (unit: [g/g]) obtained after allowing 0.900 g of a water absorbent resin to swell in a 0.9 wt % aqueous solution of sodium chloride for one hour under a load of 2.06 kPa (0.3 psi, 21 [g/cm$^2$]). Meanwhile, in the present invention, the measurement was made by changing the load conditions to 2.06 kPa (0.3 psi, 21 [g/cm$^2$]) or 4.83 kPa (0.7 psi, 50 [g/cm$^2$]).

(c) "Ext" (ERT470.2-02)

The term "Ext" is an abbreviation for Extractables, and means a water-solubilized fraction (amount of water-solubilized components). Specifically, the Ext is the value (unit: wt %) obtained by stirring 1 g of a water absorbent resin in 200 g of a 0.9 wt % aqueous solution of sodium chloride for 16 hours, and then measuring the amount of dissolved polymer by pH titration.

(d) "FSC" (ERT440.2-02)

The term "FSC" is an abbreviation for Free Swell Capacity, and means the ratio of free swelling. Specifically, the FSC is absorption capacity (unit: [g/g]) measured after immersing 0.20 g of a water absorbent resin in 0.20 g of a 0.9 wt % aqueous solution of sodium chloride for 30 minutes, without performing dehydration with a centrifuge.

(e) "Residual Monomers" (ERT410.2-02)

The term "Residual Monomers" means the amount of monomers remaining in a water absorbent resin. Specifically, the residual monomers is the value (unit: ppm) obtained by introducing 1.0 g of a water absorbent resin in 200 ml of a 0.9 wt % aqueous solution of sodium chloride, stirring the mixture for 2 hours, and then measuring the amount of monomers eluted into the aqueous solution by high performance liquid chromatography.

(f) "PSD" (ERT420.2-02)

The term "PSD" is an abbreviation for Particle Size Distribution, and means the particle size distribution measured by sieve classification. Meanwhile, the weight average particle size (D50) and the particle size distribution width are measured by a method similar to "(1) Average Particle Diameter and Distribution of Particle Diameter" described in EP No. 0349240, p. 7, lines 25-43.

(g) Other Physical Properties of Water Absorbent Resin Defined by EDANA

"pH" (ERT400.2-02) means pH of a water absorbent resin.

"Moisture Content" (ERT430.2-02) means water content percentage of a water absorbent resin.

"Flow Rate" (ERT450.2-02) means a flow-down speed of a water absorbent resin.

"Density" (ERT460.2-02) means bulk specific gravity of a water absorbent resin.

"Respirable Particles" (ERT480.2-02) means respirable dust of a water absorbent resin.

"Dust" (ERT490.2-02) means dust contained in a water absorbent resin.

(1-4) Liquid Permeability

The flow of a liquid that flows between the particles of a swollen gel under a load or without load is referred to as "liquid permeability." Representative measurement methods for this "liquid permeability" include SFC (Saline Flow Conductivity) and GBP (Gel Bed Permeability).

The term "SFC (saline flow conductivity)" means the liquid permeability of a 0.69 wt % aqueous solution of sodium chloride in 0.9 g of a water absorbent resin under a load of 0.3 psi. This is measured according to the SFC test method described in U.S. Pat. No. 5,669,894 A.

The term "GBP" means the liquid permeability of a 0.69 wt % physiological saline in a water absorbent resin under a load or under free swelling. This is measured according to the GBP test method described in WO 2005/016393.

(1-5) Others

In the present specification, the expression "X to Y" that indicates a range means "equal to or more than X and equal to or less than Y." Furthermore, the unit of weight, "t (ton)", means "metric ton", and unless otherwise specified, the unit "ppm" means "ppm by weight" or "ppm by mass". Furthermore, in the present specification, "mass" and "weight", "% by mass" and "% by weight", and "parts by mass" and "parts by weight" are synonyms, and in regard to the measurement of physical properties and the like, measurement is made at room temperature (20° C. to 25° C.)/a relative humidity of 40% to 50% unless otherwise specified. Furthermore, the term "-acid (salt)" means "-acid and/or a salt thereof", and "(meth)acryl" means "acryl and/or methacryl".

[2] METHOD FOR PRODUCING WATER ABSORBENT RESIN

(2-1) Polymerization Step

The present step is a step of polymerizing an aqueous solution containing acrylic acid and/or a salt thereof (hereinafter, referred to as "acrylic acid (salt)") as a main component, and thereby obtaining a water-containing gel-like crosslinked polymer.

(a) Monomer (Excluding Crosslinking Agent)

The water absorbent resin obtained by the present invention is usually polymerized in the state of an aqueous solution by using, as a raw material thereof (monomer), an aqueous solution containing acrylic acid (salt) as a main component. The monomer concentration (solid content concentration) of the aqueous monomer solution is usually 10% to 90% by weight, and preferably 20% to 80% by weight. Further, polymerization at a high monomer concentration (35% by weight or greater, still more preferably 40% by weight or greater, and particularly preferably 45% by weight or greater; the upper limit is the saturation concentration, still more preferably 80% by weight or less, and particularly preferably 70% by weight or less) may be mentioned as a most preferred example.

Furthermore, when the monomer is polymerized in an aqueous solution, surfactants, polymer compounds such as polyacrylic acid (salt), starch, cellulose and polyvinyl alcohol, various chelating agents, and various additives may be optionally added, in an amount of 0% to 30% by weight, and preferably 0.001% to 20% by weight, relative to the amount of the monomer.

Furthermore, it is preferable that the hydrogel obtained by polymerization of the aqueous solution have at least a portion of the acid groups of the polymer neutralized, from the viewpoint of absorption performance. The neutralization process can be carried out before polymerization (monomer), during polymerization, or after polymerization (hydrogel) of acrylic acid. However, from the viewpoints of productivity of the water absorbent resin, an enhancement of AAP (absorption against pressure) or SFC (saline flow conductivity), and the like, it is preferable to carryout neutralization before the polymerization of acrylic acid. That is, it is preferable to use neutralized acrylic acid (that is, a partially neutralized salt of acrylic acid) as a monomer.

The neutralization ratio of neutralization described above is not particularly limited, but the neutralization ratio is preferably 10% to 100% by mole, more preferably 30% to 95% by mole, still more preferably 50% to 90% by mole, and particularly preferably 60% to 80% by mole, relative to the acid group. If the neutralization ratio is less than 10% by mole, the CRC (absorption capacity without load) in particular may be markedly decreased, which is not preferable.

Furthermore, in the case of using acrylic acid (salt) as a main component in the present invention, a hydrophilic or hydrophobic unsaturated monomer other than acrylic acid (salt) (hereinafter, also referred to as "other monomer" in some cases) can also be used. There are no particular limitations on such another monomer, but examples include methacrylic acid, (anhydrous) maleic acid, 2-(meth)acrylamido-2-methylpropanesulfonic acid, (meth)acryloxyalkanesulfonic acid, N-vinyl-2-pyrrolidone, N-vinylacetamide, (meth)acrylamide, N-isopropyl (meth)acrylamide, N,N-dimethyl (meth)acrylamide, 2-hydroxyethyl (meth) acrylate, methoxypolyethylene glycol (meth)acrylate, polyethylene glycol (meth)acrylate, stearyl acrylate, and salts thereof, or the like. When these other monomers are used, the use amount is not particularly limited as long as the use amount is to the extent that the absorption characteristics of the water absorbent resin thus obtainable are not impaired, but the use amount is preferably 50% by weight or less, and more preferably 20% by weight or less, relative to the total weight of monomers. Further, when these other monomers are optionally used, the lower limit of the use amount is appropriately determined in accordance with the type, purpose or effect of the monomer and is not particularly limited; however, the lower limit of the use amount is about 1% by weight relative to the total weight of monomers.

(b) Salt of Neutralization

There are no particular limitations on the basic substance that is used for the neutralization of acrylic acid as a monomer or the polymer (hydrogel) after polymerization, but a monovalent basic substance including an alkali metal hydroxide such as sodium hydroxide, potassium hydroxide and lithium hydroxide, and a (hydrogen) carbonate such as sodium (hydrogen) carbonate and potassium (hydrogen) carbonate, and the like are preferred, or sodium hydroxide is particularly preferred. Furthermore, the temperature at the time of neutralization (neutralization temperature) is not particularly limited, and the temperature is preferably 10° C. to 100° C., and more preferably 30° C. to 90° C. Meanwhile, in regard to the neutralization treatment conditions and the like other than those described above, the conditions and the like disclosed in WO 2007/028751 and U.S. Pat. No. 6,388,000 are preferably applied to the present invention.

(c) Crosslinking Agent (Internal Crosslinking Agent)

In the present invention, it is particularly preferable to use a crosslinking agent (hereinafter, also referred to as "internal crosslinking agent" in some cases) from the viewpoint of absorption performance of water absorbent resin thus obtained. Examples of the internal crosslinking agent that can be used include a compound having two or more polymerizable double bonds per molecule, and a polyfunctional compound having two or more functional groups per molecule that are capable of reacting with carboxyl groups and forming a covalent bond therewith. For example, one or more kinds of a polymerizable crosslinking agent capable of polymerizing with acrylic acid, a reactive crosslinking agent capable of reacting with a carboxyl group, and a crosslinking agent having the two functions thereof in combination, may be exemplified. Specifically, the polymerizable crosslinking agent may be, for example, a compound having at least two polymerizable double bonds in the molecule, such as N,N'-methylenebisacrylamide, (poly)ethylene glycol di(meth)acrylate, (polyoxyethylene)trimethylolpropane tri(meth)acrylate, or poly(meth)aryloxyalkane. Furthermore, examples of the reactive crosslinking agent include a polyglycidyl ether such as ethylene glycol diglycidyl ether; a crosslinking agent capable of covalent bonding, such as a polyhydric alcohol such as propanediol, glycerin, or sorbitol; and a crosslinking agent capable of ionic bonding, such as a polyvalent metal compound such as an aluminum salt. Among these, from the viewpoint of absorption performance, a polymerizable crosslinking agent capable of polymerizing with acrylic acid is preferred, and particularly, acrylate-type, aryl-type or acrylamide-type polymerizable crosslinking agent is suitably used. These internal crosslinking agents may be used alone, or two or more kinds may be used in combination. The use amount of the internal crosslinking agent described above is preferably 0.001% to 5% by mole, more preferably 0.005% to 2% by mole, still more preferably 0.01% to 1% by mole, and particularly preferably 0.03% to 0.5% by mole, from the viewpoint of the physical properties, relative to the monomer described above excluding the crosslinking agent.

(d) Other Trace Components

In the present invention, from the viewpoints of color tone stability and residual monomers, the content of protoanemonin and/or furfural in acrylic acid is preferably 0 ppm to 10 ppm, more preferably 0 ppm to 5 ppm, and still more preferably 0 ppm to 1 ppm. Furthermore, also for the same reason, the content of aldehyde components other than furfural and/or maleic acid in acrylic acid is preferably 0 ppm to 5 ppm, more preferably 0 ppm to 3 ppm, still more preferably 0 ppm to 1 ppm, and particularly preferably 0 ppm (at or below detection limit). Meanwhile, examples of the aldehyde components other than furfural include benzaldehyde, acrolein, acetaldehyde, and the like. Further, for the purpose of reducing the residual monomers, the content of acrylic acid dimer is preferably 0 ppm to 500 ppm, more preferably 0 ppm to 200 ppm, and still more preferably 0 ppm to 100 ppm.

In the present invention, it is preferable that a methoxyphenol compound be included in the unsaturated monomer, and it is more preferable that p-methoxyphenol be included, from the viewpoint of polymerization stability. The content of the methoxyphenol compound is preferably 1 ppm to 250 ppm, more preferably 5 ppm to 200 ppm, still more preferably 10 ppm to 160 ppm, and particularly preferably 20 ppm to 100 ppm, relative to the monomer (acrylic acid).

(e) Other Component in Aqueous Monomer Solution

In order to improve various physical properties of the water absorbent resin obtained by the present invention, the following substance can be added as an optional component to the aqueous monomer solution. That is, a water-soluble resin or a water absorbent resin, such as starch, polyacrylic acid (salt), polyvinyl alcohol, or polyethyleneimine can be added in an amount of, for example, 0% to 50% by weight, preferably 0% to 20% by weight, more preferably 0% to 10% by weight, and still more preferably 0% to 3% by weight, relative to the monomer. Here, the lower limit of the additive amount of the optional component when the optional component described above is added is appropriately determined in accordance with the type, purpose and effect of the optional components and is not particularly limited, but the lower limit is preferably about 0.001% by weight relative to the monomer. Furthermore, additives such as various expanding agents (carbonates, azo compounds, air bubbles, and the like), surfactants, various chelating agents, hydroxycarboxylic acids, and reducing inorganic salts can be added in an amount of, for example, 0% to 5% by weight, and preferably 0% to 1% by weight, based on the monomer. Here, the lower limit of the amount of the additive when the additive described above is added is appropriately determined in accordance with the type, purpose and effect of the additive and is not particularly limited, but the lower limit is preferably about 0.001% by weight relative to the monomer.

Among these, when it is intended to suppress coloration over time of the water absorbent resin (enhancement of color tone stability in long-term storage under high temperature and high humidity) or to enhance urine resistance (prevention of gel deterioration), a chelating agent, a hydroxycarboxylic acid, or a reducing inorganic salt is preferably used, and a chelating agent is particularly preferably used. The use amount in this case is preferably 10 ppm to 5,000 ppm, more preferably 10 ppm to 1,000 ppm, still more preferably 50 ppm to 1,000 ppm, and particularly preferably 100 ppm to 1,000 ppm, relative to the water absorbent resin. Meanwhile, in regard to the chelating agent, hydroxycarboxylic acid and reducing inorganic salt, the compounds disclosed in WO 2009/005114 A, EP 2 057 228 B, and EP 1 848 758 B are used.

(f) Polymerization Initiator

The polymerization initiator used in the present invention is appropriately selected depending on the polymerization form, and is not particularly limited. Examples include a thermally degradable type polymerization initiator, a photodegradable type polymerization initiator, a redox-type polymerization initiator, and the like. Specific examples of the thermally degradable type polymerization initiator include persulfates such as sodium persulfate, potassium persulfate, and ammonium persulfate; peroxides such as hydrogen peroxide, t-butyl peroxide, and methyl ethyl ketone peroxide; and azo compounds such as 2,2'-azobis(2-amidinopropane)dihydrochloride, and 2,2'-azobis[2-(2-imidazolin-2-yl)propane]dihydrochloride, and the like. Furthermore, examples of the photodegradable type polymerization initiator include benzoin derivatives, benzyl derivatives, acetophenone derivatives, benzophenone derivatives, azo compounds, and the like. Furthermore, examples of the redox-type polymerization initiator include systems obtained by combining the persulfates or peroxides described above with reducing compounds such as L-ascorbic acid and sodium hydrogen sulfite. According to a preferred embodiment, the thermally degradable type polymerization initiator and the photodegradable type polymerization initiator described above may be used in combination. The use amount of these polymerization initiators is preferably 0.0001% to 1% by mole, and more preferably 0.001% to 0.5% by mole, relative to the monomer described above. If the use amount of the polymerization initiator is larger than 1% by mole, it is not preferable because coloration of the water absorbent resin may occur. Furthermore, if the use amount of the polymerization initiator is less than 0.0001% by mole, it is not preferable because there is a risk that the amount of residual monomers may increase.

Meanwhile, instead of using the polymerization initiator described above, polymerization may also be carried out by irradiating an active energy ray such as a radiation, an electron beam, or ultraviolet radiation. Alternatively, polymerization may also be carried out by using this active energy ray and the polymerization initiator in combination.

(g) Polymerization Method (Crosslink-Polymerization Step)

In the present invention, at the time of polymerizing the aqueous monomer solution described above, aqueous solution polymerization or reverse phase suspension polymerization is usually employed from the viewpoints of the absorption performance of the water absorbent resin obtained, the ease of polymerization control, or the like, but preferably aqueous solution polymerization, and more preferably continuous aqueous solution polymerization is employed. Among these, this method is preferably applied to the production in a huge scale with a large production output per one line of the water absorbent resin. The production output is 0.5 [t/hr] or greater, more preferably 1 [t/hr] or greater, still more preferably 5 [t/hr] or greater, and particularly preferably 10 [t/hr] or greater.

Furthermore, preferred forms of the aqueous solution polymerization include continuous belt polymerization (U.S. Pat. No. 4,893,999 A, U.S. Pat. No. 6,241,928 A, US 2005/215734 A, and the like), and continuous kneader polymerization (U.S. Pat. No. 6,987,151 A, U.S. Pat. No. 670,141 A, and the like).

In regard to the continuous aqueous solution polymerization described above, high temperature initiated polymerization in which the polymerization initiation temperature is set to 30° C. or higher, preferably 35° C. or higher, more preferably 40° C. or higher, still more preferably 50° C. or higher, and particularly preferably 60° C. or higher (the upper limit is the boiling point); or the high monomer concentration polymerization described above, may be mentioned as one of most preferred examples. Meanwhile, the polymerization initiation temperature described above is defined as the temperature of the liquid immediately before the supply of the aqueous monomer solution to a polymerization reactor, but the conditions and the like disclosed in U.S. Pat. No. 6,906,159 A, U.S. Pat. No. 7,091,253 and the like can be preferably applied to the present invention.

Furthermore, from the viewpoints of an enhancement of the physical property of the water absorbent resin obtained and of drying efficiency, it is preferable to obtain a water absorbent resin at a higher solid content concentration by evaporating moisture at the time of polymerization. The extent of increase in the solid content concentration from the aqueous monomer solution (solid content of hydrogel after polymerization–solid content of monomer before polymerization) is preferably 1% by weight or greater, more preferably 2% to 40% by weight, and still more preferably 3% to 30% by weight. However, a range in which a water-containing gel-like crosslinked polymer having a solid content of 80% by weight or less as will be disclosed below is obtained is preferred.

These polymerization can be carried out in an air atmosphere, but from the viewpoint of preventing coloration, the polymerization is preferably carried out in an inert gas atmosphere such as nitrogen or argon (for example, oxygen concentration: 1% by volume or less). Furthermore, it is preferable to purge the dissolved oxygen in the monomer or the solution containing the monomer with an inert gas (for example, dissolved oxygen concentration: less than 1 mg/L), and then to perform polymerization. Furthermore, the polymerization can be carried out under any pressure, such as under reduced pressure, under normal pressure, or under pressure.

(2-2) Grain Refining Step for Water-Containing Gel-Like Crosslinked Polymer (Gel-Crushing Step)

The present step is a step of crushing the water-containing gel-like crosslinked polymer obtained in the polymerization step described above, and thereby obtaining a particulate water-containing gel-like crosslinked polymer (hereinafter, referred to as "particulate hydrogel").

The hydrogel obtained in the polymerization step described above may be directly subjected to drying, but preferably, the hydrogel is optionally subjected to gel-crushing, during polymerization or after polymerization, by using a crusher (a kneader, a meat chopper, a cutter mill, or the like) and is converted to a particulate form, in order to solve the problem described above. That is, a hydrogel grain refining (hereinafter, also referred to as "gel-crushing") step may further be included between the polymerization step based on continuous belt polymerization or continuous kneader polymerization, and the drying step. Meanwhile, even the case in which the gel is subjected to grain refining by dispersion in a solvent at the time of polymerization, such as reverse phase suspension polymerization, is also meant to be included in the grain refining of the present invention (grain refining of the polymerization step), but suitably, the gel is gel-crushed by using a crusher.

In regard to the temperature of the hydrogel at the time of gel-crushing, the hydrogel is kept warm or heated preferably to 40° C. to 95° C., and more preferably 50° C. to 80° C., in view of the physical properties. The weight average particle size (D50) of the particulate hydrogel after gel-crushing is preferably 0.5 mm to 4 mm, more preferably 0.5 mm to 3 mm, and still more preferably 0.3 mm to 2 mm. When the weight average particle size (D50) of the particulate hydrogel described above is in the range described above, it is preferable because drying can be efficiently carried out. Furthermore, the proportion of the particulate hydrogel having a particle size of 5 mm or larger is preferably 0% to 10% by weight, and more preferably 0% to 5% by weight, relative to the total amount of the particulate hydrogel. Here, the particle size of the particulate hydrogel is measured by using the wet classification method described in paragraph [0091] of JP-A No. 2000-63527.

(2-3) Drying Step

The water-containing gel-like crosslinked polymer obtained in the polymerization step described above, or the particulate hydrogel obtained in the gel-crushing step can be dried up to a desired resin solid content. There are no particular limitations on the method, but various drying methods such as, for example, heating and drying, hot air drying, drying under reduced pressure, infrared drying, microwave drying, drum dryer drying, dehydration drying by azeotropy with a hydrophobic organic solvent, and high humidity drying by using water vapor at a high temperature, can be employed. Among these drying methods, hot air drying is preferred; hot air drying by a gas having a dew point temperature of 0° C. to 100° C. is more preferred; hot air drying by a gas having a dew point temperature of 20° C. to 90° C. is still more preferred; and particularly, ventilated band drying is preferred. Furthermore, the drying temperature (equivalent to the hot air temperature) is also not particularly limited, and the drying temperature is preferably 100° C. to 300° C., and more preferably 150° C. to 250° C. However, in order to achieve a balance between an improvement of the physical property of the water absorbent resin obtained and the degree of whiteness, it is preferable that the drying temperature be 165° C. to 230° C., and the drying time be within 50 minutes, more preferably 20 minutes to 40 minutes. If the drying temperature and drying time are not in the ranges described above, there is a risk of causing a decrease in the absorption capacity without load (CRC) of the water absorbent resin, an increase in the extractables, or a decrease in the degree of whiteness, which is not preferred.

Furthermore, the resin solid content that is determined from the dry weight reduction of the particulate hydrogel (change in the weight when 1 g of a water absorbent resin powder or particle is heated for 3 hours at 180° C.) is preferably 80% by weight or greater, more preferably 85% to 99% by weight, still more preferably 90% to 98% by weight, and particularly preferably 92% to 97% by weight. In the present drying step, a dried product in which the resin solid content has been adjusted to the range described above is obtained. The resin solid content of the dried product substantially corresponds to the resin solid content of the water absorbent resin powder before being surface cross-linked, and is preferably applied as the resin solid content for the classification step in the present invention.

When the moisture content of the dried product obtained in the present step is high, that is, when the resin solid content is low, for example, when the resin solid content is less than 80% by weight, a decrease in the absorption capacity (per the resin solid content), aggregation of the water absorbent resin in a subsequent step such as the surface crosslinking step, a decrease in the physical property, and further a decrease in conveyance property may be observed. On the other hand, when the moisture content of the dried product obtained in the present step is low, that is, the resin solid content is high, for example, when the resin solid content is greater than 99% by weight, the water absorbent resin may not be obtained unless a long time is taken as the drying time, and also, deterioration of the water absorbent resin or a decrease in the powder characteristics (prevention of static charge, impact resistant stability, deterioration of the physical property at the time of transport, and the like) may be observed.

Moisture (moisture content) in the water absorbent resin becomes an inhibitory factor of classification, but it is preferable to produce a water absorbent resin having a moisture content in the predetermined range described above, rather than to produce a water absorbent resin in an absolute dry state with a moisture content of less than 1% by weight. Since such a water absorbent resin can exhibit a better effect through a classification step, it can be preferably applied to a method for producing a water absorbent resin, which includes a classification step of a water absorbent resin having a moisture content in the range described above.

Furthermore, in order to promote a reduction of residual monomers of the water absorbent resin obtained, prevention of gel deterioration (urine resistance), and prevention of yellowing, it is preferable to shorten the time taken from after the completion of polymerization to the initiation of drying. That is, regardless of the presence or absence of the gel-crushing step described above, it is preferable to adjust the time period from the point of completion of polymerization to the initiation of drying, to one hour or less, more preferably 0.5 hours or less, and still more preferably 0.1 hours or less. Furthermore, during this period, the temperature of the water-containing gel-like crosslinked polymer is preferably controlled to 50° C. to 80° C., and still more preferably 60° C. to 70° C. When the temperature is controlled to this temperature range, a reduction of residual monomers or low coloration can be achieved.

(2-4) Pulverization Step

The present step is a step for pulverizing the dried product obtained in the drying step described above, and is an optional step in the present invention. The pulverizer that can be used in the present step is not particularly limited, and any conventionally known pulverizer can be used. Specific examples include a roll mill, a hammer mill, a roll granulator, a jaw crusher, a gyratory crusher, a cone crusher, a roll crusher, a cutter mill, and the like. Among these, from the viewpoint of particle size control, it is preferable to use a multistage roll mill or a roll granulator. Meanwhile, in the case of drying the particulate water-containing gel-like polymer (particularly drying by using a ventilated band type dryer), the particulate hydrogel aggregates during the drying period, and a block-like dried product (aggregate) may be formed. In this case, it is desirable to perform coarsely crushing of the aggregate (an operation of breaking aggregation).

Through the pulverization step, the dried product obtained in the drying step described above is pulverized, and thus a pulverized dried product (an irregularly shaped crushed water absorbent resin powder) is obtained. Since the physical property of the water absorbent resin powder is improved by the pulverization step, the pulverization step is preferably applied.

From the viewpoint of enhancing the physical property of the water absorbent resin obtained in the present step, it is preferable to control the particle size to obtain the particle size described below. That is, the weight average particle size (D50) of the water absorbent resin powder (before surface crosslinking) is preferably 200 μm to 600 μm, more preferably 200 μm to 550 μm, still more preferably 250 μm to 500 μm, and particularly preferably 350 μm to 450 μm. Furthermore, the proportion of fine particles that pass through a sieve (JIS standard sieve) having a mesh opening size of 150 μm (having a particle size of less than 150 μm) is preferably 0% to 5% by weight, more preferably 0% to 3% by weight, and still more preferably 0% to 1% by weight, relative to the total amount of the water absorbent resin powder. Furthermore, the proportion of giant particles that do not pass through a sieve (JIS standard sieve) having a mesh opening size of 850 μm (having a particle size of 850 μm or greater) is preferably 0% to 5% by weight, more preferably 0% to 3% by weight, and still more preferably 0% to 1% by weight, relative to the total amount of the water absorbent resin powder. Further, the logarithmic standard deviation ($\sigma\zeta$) of the particle size distribution is preferably 0.20 to 0.40, more preferably 0.25 to 0.39, and still more preferably 0.27 to 0.38. These physical property values are measured by using standard sieves and by the methods disclosed in, for example, WO 2004/069915 A or EDANA-ERT420.2-02 ("PSD"). Furthermore, in the present invention, the proportion of particles having a particle size of equal to or greater than 150 μm and less than 850 μm is preferably 95% by weight or greater, and more preferably 98% by weight or greater, relative to the total amount of the water absorbent resin powder, and the upper limit is 100% by weight. It is preferable to surface crosslink a water absorbent resin powder having the proportion described above. Furthermore, also for the particle size of the water absorbent resin after being surface crosslinked, and further the particle size of the final product, the same particle size as that of the water absorbent resin powder before being surface crosslinked described above is applied.

(2-5) Classification Step

The present step is a step of adjusting the particle size to a particular particle size (weight average particle size (D50), particle size distribution, or the like), in order to improve the physical property of the water absorbent resin. Meanwhile, the particle size control is not limited to the present classification step, and can be appropriately adjusted in a polymerization step (particularly, reverse phase suspension polymerization), a pulverization step, a fine powder collection step, a granulation step, and the like. Hereinafter, the particle size will be defined by standard sieves (JIS Z8801-1 (2000) or equivalents thereof).

In the present step, when sieve classification is carried out, and at least one of the following constitutions (i) and (ii) is carried out, the physical property (particularly, liquid permeability) of the surface crosslinked water absorbent resin is improved. Furthermore, even in continuous production for a long time period, a decrease in the physical property (particularly, liquid permeability) can be reduced. Meanwhile, evaluation of physical property values in continuous production is carried out in the Examples described below, and generally in an operation for a long time, it is observed that the physical property tends to deteriorate with a lapse of time. However, such a tendency is not seen in the present invention, and such an effect is markedly exhibited at the time of industrial continuous production of a water absorbent resin having high liquid permeability, particularly at the time of industrial continuous production (for example, continuous production for 24 or more hours at 1 [t/hr]) of a water absorbent resin having an SFC (saline flow conductivity) of $10[\times 10^{-7}\ cm^3 \cdot s \cdot g^{-1}]$ or more.

The water absorbent resin powder obtained in the pulverization step described above is classified before and/or after the surface crosslinking step that will be described below, and preferably classified before and after the surface crosslinking step, and particularly preferably, the water absorbent resin powder is sieve classified. Through the classification step, a classified product (water absorbent resin powder) having a desired particle size described above is obtained. When the classification step is carried out before the surface crosslinking step, the final product can be adjusted to have a particle size in the desired range, which is preferable. Furthermore, when the classification step is carried out after the surface crosslinking step, aggregate particles having a particle size other than the desired size, which are generated at the time of mixing of a surface crosslinking agent or at the time of heating treatment, or fine particles having a particle size other than the desired size, which are generated by physical and mechanical destruction in these steps, are removed by classification and further disintegrated, and thereby a water absorbent resin having excellent performance can be produced, which is preferable.

(a) Conventional Classification Method

Methods for sieve classification of a water absorbent resin are disclosed in, for example, Patent Literature 24 to 29 described below. These Patent Literature 24 to 29 suggest neither the constitutions (i) to (v) described below, nor the problems or effects of the present invention. Furthermore, Patent Literature 1 to 23 described above do not disclose the classification method of the present invention.

Furthermore, Patent Literature 30 (International filing date: Sep. 11, 2009), which was internationally filed before the priority date of the present application, discloses that removal of electricity is carried out in a classification step for a water absorbent resin, but does not disclose or suggest the constitutions (i) to (v) of the present invention as described below.
Patent Literature 24: U.S. Pat. No. 6,164,455 A
Patent Literature 25: WO 2006/074816 A
Patent Literature 26: WO 2008/037672 A
Patent Literature 27: WO 2008/037673 A
Patent Literature 28: WO 2008/037675 A
Patent Literature 29: WO 2008/123477 A
Patent Literature 30: WO 2010/032694 A (b) Production Method, Classification Method, and Liquid Permeability Enhancing Method of the Present Invention The method for producing a water absorbent resin according to the present invention is a method for producing a water absorbent resin, which includes a polymerization step of polymerizing an aqueous solution of acrylic acid (salt) to obtain a water-containing gel-like crosslinked polymer; a drying step of drying the water-containing gel-like crosslinked polymer to obtain a water absorbent resin powder; a classification step of classifying the water absorbent resin powder; and a surface crosslinking step of surface crosslinking the water absorbent resin powder, and the method needs to satisfy any one or more of the following constitutions (i) and (ii). Furthermore, it is preferable that the method satisfy the following constitutions (iii) to (v), in addition to the following constitutions (i) and/or (ii).

(i) The stretch tension (tension) of the metal sieve mesh used in the classification step is from 35 [N/cm] to 100 [N/cm].

(ii) An airbrush is used below the metal sieve mesh used in the classification step.

(iii) A tapping material is used below the metal sieve mesh used in the classification step.

(iv) A classification aid particle is used, and the classification aid particle and a fine powder (fine particle) of the water absorbent resin are removed.

(v) Damage monitoring of a metal sieve mesh that is used in the classification step is carried out (preferably by electrical detection using ultrasonic waves or high frequency waves, particularly by an AE method).

Furthermore, it is preferable that the metal sieve be further heated or kept warm. It is preferable that the metal sieve be removed of electricity. Classification is preferably carried out under reduced pressure conditions.

Hereinafter, the constitutions (i) to (v) will be described in detail.

(i) Stretch Tension (Tension)

The term "stretch tension (tension)" according to the present invention means the load imposed when the metal sieve mesh used in the classification step is stretched. The tension of the classifying mesh (metal mesh) of the present invention is preferably 35 [N/cm] or greater, more preferably 40 [N/cm] or greater, still more preferably 45 [N/cm] or greater, and particularly preferably 50 [N/cm] or greater. Furthermore, the upper limit of the tension is preferably 100 [N/cm] or less, more preferably 80 [N/cm] or less, and still more preferably 60 [N/cm] or less. When the tension describe above is 35 [N/cm] or greater, a decrease in the classification efficiency of the water absorbent resin powder can be prevented, and liquid permeability of the water absorbent resin obtained is improved. Furthermore, when the tension described above is 100 [N/cm] or less, since durability of the metal mesh can be secured, continuous operation is enabled. Meanwhile, the measurement of the tension described above is carried out by using a tension meter at the center of the sieve when the metal mesh is stretched in the classifying sieve. The principle of measurement is "Mechanical measuring of the fabric's sagging under a constant force." The tension meter described above is such that various products are commercially available, and for example, products are sold from Tekomat SE and the like. In the present invention, those commercially available products can be used.

In the method according to the present invention for producing a water absorbent resin which includes a classification step, it was found that the stretch tension (tension) of the metal sieve mesh affects the physical property of the water absorbent resin, particularly the physical property of the water absorbent resin after being surface crosslinked, in particular the absorption capacity under load (for example, AAP) or liquid permeability (for example, SFC). It was found that such stretch tension (tension) also affects the case where the organic surface crosslinking agent and the inorganic surface crosslinking agent are used in the (2-6) surface crosslinking step described below, and further, an irregularly shaped crushed water absorbent resin including the (2-4) pulverization step described above. Thus, the inventors completed the present invention.

The technologies for enhancing the absorption capacity under load or liquid permeability have been suggested in many literature such as Patent Literature 1 to 23 described above; however, in these related art literature, there is no disclosure of a technology which paid attention to the classification step, and in particular, to the stretch tension (tension) of the metal sieve mesh. Meanwhile, since not only an enhancement of the above-mentioned physical property (particularly, the absorption capacity under load or liquid permeability), but also an increase in the productivity of a water absorbent resin having the particular physical property described above or prevention of operation trouble (stopped production due to the destruction of the sieve mesh) can be promoted by the control of the stretch tension (tension) according to the present invention, it is more preferable. When the stretch tension (tension) is controlled to a certain extent, there is less damage to the sieve mesh during continuous operation, and continuous operation for a long time is enabled. Conventionally, there have been occasions in which when continuous operation for a long time is implemented, a rapid decrease in the physical property or a change in the particle size is recognized. However, when the cause was investigated, it was found that damage of the sieve in the classification step is a cause, and the problem could be solved by controlling tension in the classification step.

Furthermore, in the case of using one or plural classifying meshes (metal sieve mesh) in a single classification step (classifying apparatus), and/or in the case of performing classification in two or more plural classification steps (for example, classification step 1 (before the surface crosslinking step), classification step 2 (after the surface crosslinking step), and classification step 3 (after the surface crosslinking step) before and after the surface crosslinking step) by using one or plural classifying meshes (metal sieve mesh), the control of the stretch tension (tension) of the metal sieve mesh need be implemented in some of the metal sieve mesh, or in all of the metal sieve mesh. That is, in the classification step that are carried out before the surface crosslinking step and/or after the surface crosslinking step, it is preferable to control the stretch tension (tension) in 30% or more of the total number of the metal sieve mesh used in the classification step, and preferably, in sequence, in 50% or more, 70% or more, 80% or more, and 90% or more of the metal sieve mesh. It is most preferable to control the stretch tension (tension) in substantially 100% of the metal sieve mesh.

The method of stretching the metal mesh is not particularly limited, but a metal mesh may be placed over a sieve frame, and while one edge of the metal mesh is pulled with a jack or the like to be planar, the metal mesh may be fixed to the sieve frame by soldering or with bolts. The tension according to the present invention is defined as the tension at the time of fabrication of a metal sieve. For the metal mesh, a mesh made of a metal as will be described below, preferably a mesh made of stainless steel (preferably, SUS304, SUS316) or made of Magnestain, is used.

The tension of the classifying mesh described above may also be used in combination with the following constitution (ii) or (iii). Further, the tension may be used in further combination with the constitutions (iv) and/or (v).

(ii) Airbrush (Air Knife)

From the viewpoints of the classification efficiency for the water absorbent resin powder and the physical property of the water absorbent resin obtained, an airbrush (air knife) is used below the metal sieve mesh described above. According to the present invention, the airbrush refers to an instrument which sprays gas (air) such as compressed air, and is also called an air knife.

Examples of the airbrush (air knife) described above include an air jet cleaner, an air jet brush cleaner, and the like.

In regard to the method according to the present invention for producing a water absorbent resin including a classification step, it was found that an airbrush (air knife) affects the physical property of the water absorbent resin, particularly the physical property of the water absorbent resin after being surface crosslinked, in particular, the absorption capacity under load (for example, AAP) or liquid permeability (for example, SFC). It was found that such an airbrush (air knife) affects the case where the organic surface crosslinking agent and the inorganic surface crosslinking agent are used in the (2-6) surface crosslinking step described below, and further, an irregularly shaped crushed water absorbent resin including the (2-4) pulverization step described above. Thus, the inventors completed the present invention.

Technologies for enhancing the absorption capacity under load or liquid permeability have been suggested in many Literature such as Patent Literature 1 to 23 described above; however, in these related art Literature, there is no disclosure of a technology which paid attention to the classification step, and in particular, an airbrush (air knife). Meanwhile, since not only an enhancement of the above-mentioned physical property (particularly, the absorption capacity under load or liquid permeability), but also an increase in the productivity of a water absorbent resin having the particular physical property described above can be promoted by the control of the airbrush (air knife) according to the present invention, it is still more preferable.

Furthermore, in the case of using plural classifying meshes (metal sieve mesh) in a single classification step (classifying apparatus), and/or in the case of performing classification in two or more plural classification steps (for example, classification step 1 (before the surface crosslinking step) or classification step 2 (after the surface crosslinking step) before and after the surface crosslinking step), the use of an airbrush (air knife) may be implemented in some of the sieves, or may be implemented in all of the sieves. However, the airbrush is preferably used with at least some of the sieves (sieves having a mesh opening size of 300 μm or less), and it is preferable to use the airbrush (air knife) with 30% or more of all the sieves, and preferably, in sequence, in 50% or more, 70% or more, 90% or more, and 100% of all the sieves.

When the tapping material is used above the metal sieve mesh, or the tapping material is not used, there occurs a problem of deterioration, particularly deterioration over time, of the physical property of the water absorbent resin (for example, liquid permeability), or an increase in fine powder or powder dust, which is not preferable. However, in this case, air that is sprayed from a rotating nozzle arm may be sprayed strongly from the back surface (particularly, the back surface of a circular sieve) of the metal sieve mesh, to perform cleaning.

The airbrush of the present invention is particularly preferably used at the time of classifying fine powder, and it is preferable that the airbrush be installed below a sieve having a mesh opening size of 200 μm or less, and more preferably a sieve having a mesh opening size of 150 μm or less. The lower limit of the mesh opening size of the sieve described above is preferably 30 μm or greater, more preferably 45 μm or greater, and still more preferably 75 μm or greater. The airbrush is preferably used for the classification of fine powder as a substitute for the tapping material describe above, and can enhance the liquid permeability (SFC or GBP) of the water absorbent resin obtained.

From the viewpoint that the water absorbent resin powder can stably retain excellent physical property, and the blocking phenomenon can be suppressed, it is preferable that the airbrush of the present invention use dry air as primary air and secondary air. The dew point of the dry air is preferably 0° C. or lower, more preferably −30° C. or lower, still more preferably −35° C. or lower, and particularly preferably −40° C. or lower. Examples of methods of controlling the dew point include a method of using a membrane dryer, a method of using a cooling adsorption dryer, a method of using a diaphragm dryer, and methods of using these dryers in combination. In the case of using an adsorption dryer, the adsorption dryer may be a heating regeneration type, a non-heating regeneration type, or a non-regeneration type.

Furthermore, heated air may also be used, other than dry air. The heating method for the heated air is not particularly limited, but air may be directly heated by using a heat source, or may be indirectly heated by heating an apparatus or pipes. The temperature of the heated air is preferably 30° C. or higher, more preferably 50° C. or higher, and still more preferably 70° C. or higher.

The airbrush described above is preferably used in combination with the tension of the constitution (i) described above. Further, the airbrush is preferably used in further combination with the constitution (iv) and/or (v).

(iii) Tapping Material

From the viewpoints of the classification efficiency of the water absorbent resin powder and the physical property of the water absorbent resin obtained, a tapping material is used below the metal sieve mesh described above. A tapping material refers to an elastic material that is used to prevent clogging of a sieving apparatus, and for the shape of the tapping material, any shape that is capable of rolling, such as a sphere, a spheroid, or a polyhedral, can be utilized. Preferably, at least one selected from a tapping ball (spherical), a tapping block (spherical) and a tapping brush is used, and more preferably, a tapping ball or a tapping block, still more preferably a tapping ball, is used. Meanwhile, when the tapping material is used above the metal sieve mesh, or the tapping material is not used, there may occur a problem of deterioration, particularly deterioration over time, of the physical property of the water absorbent resin (for example, liquid permeability), or an increase in fine powder or powder dust, which is not preferable.

In the present invention, it was found that in the method for producing a water absorbent resin including a classification step, a tapping material (preferably, a heated tapping material) affects the physical property of the water absorbent resin, particularly the physical property of the water absorbent resin after being surface crosslinked, in particular, the absorption capacity under load (for example, AAP) or liquid permeability (for example, SFC). It was found that such a tapping material affects the case where the organic surface crosslinking agent and the inorganic surface crosslinking agent are used in the (2-6) surface crosslinking step described below, and further, an irregularly shaped crushed water absorbent resin including the (2-4) pulverization step described above. Thus, the inventors completed the present invention.

The technologies of enhancing the absorption capacity under load or liquid permeability have been suggested in many literature such as Patent Literature 1 to 23 described above; however, in these related art literature, there is no disclosure of a technology which paid attention to the classification step, and in particular, the tapping material. Furthermore, not only the physical property described above (particularly, the absorption capacity under load or liquid permeability) are enhanced, but also productivity of a water absorbent resin having the particular physical properties described above can be enhanced by the control of the tapping material of the present invention, and therefore, it is still more preferable.

Further, in the case of using plural classifying meshes (metal sieve meshes) in a single classification step (classifying apparatus), and/or in the case of performing classification in two or more plural classification steps (for example, classification step 1 (before the surface crosslinking step) and classification step 2 (after the surface crosslinking step) before and after the surface crosslinking step), the tapping material may be used with some of the sieves, or may be used with all of the sieves. However, it is preferable to use the tapping material with at least some of the sieves (sieves having a mesh opening size of 300 μm or less), and preferable to use the tapping material with 30% or more of all the sieves, and in sequence, with 50% or more, 70% or more, 90% or more, and 100% of all the sieves.

The method of using the tapping material of the present invention below a metal sieve mesh is not particularly limited, but for example, a method of further providing, below the metal sieve mesh, a metal sieve mesh having a mesh opening size equal to or larger than the mesh opening size of the metal sieve mesh, or a punching metal having a hole diameter equal to or larger than the mesh opening size of the metal sieve mesh, and packing a tapping material (preferably, a tapping ball or a tapping block) on this metal sieve mesh or punching metal, may be used. From the viewpoint of classification efficiency, it is preferable to use the tapping material on a punching metal.

The tapping material described above is preferably made of a resin, and examples thereof include natural rubber, urethane, chloroprene rubber, a silicone resin, and the like. Among these, it is preferable to use a white or milky white tapping material, particularly natural white rubber, white urethane, or the like, in consideration of adherence, incorporation or the like of the tapping material to white water absorbent resins. Meanwhile, the compressive elastic modulus (Young's modulus) of these resins is preferably 0.05 GPa to 1.0 GPa, and more preferably 0.06 GPa to 0.5 GPa.

Further, the size and shape of the tapping material may be appropriately determined in accordance with desired physical properties of the water absorbent resin, but the shape is preferably a block shape or a spherical shape, while the size (diameter) is preferably 5 mm to 200 mm, still more preferably 10 mm to 100 mm, and particularly preferably 20 mm to 60 mm. Furthermore, when the size is in the ranges described above, tapping balls or taping blocks having different sizes may be used in combination. Meanwhile, when a tapping block is used, the volume is calculated in terms of the volume of a sphere, and thus the size is determined.

In the present invention, it is preferable to use plural tapping materials (tapping balls, tapping blocks or the like). The use amount of the tapping material of the present invention is defined as the cross-sectional area of tapping balls relative to the area of the metal sieve mesh, and the amount is preferably 1% or greater, and preferably, in sequence, 5% or greater, 10% or greater, 15% or greater, and 20% or greater. The upper limit is preferably less than the closest packing in consideration of the gaps between the tapping balls, and more preferably 70% or less. The use amount may be appropriately determined in this range.

Figure 2:
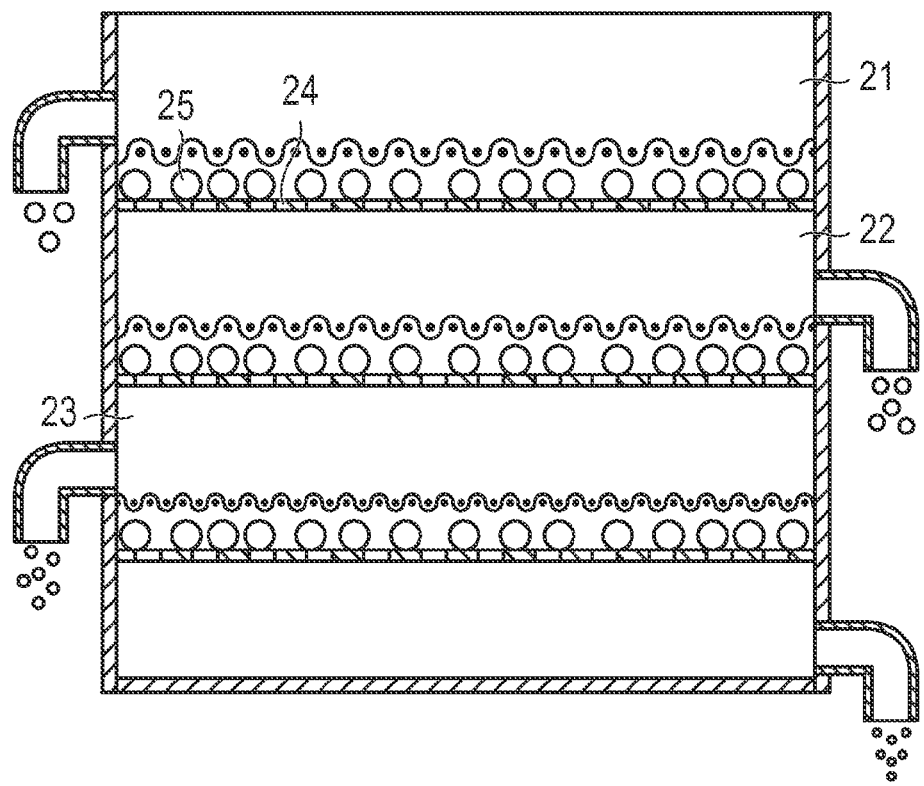
FIG. 2 is a schematic cross-sectional diagram, viewed from a lateral side, of a sieve classifying apparatus provided with tapping balls on a punching metal disposed below a metal sieve mesh.

The water absorbent resin powder that has been classified by using a tapping material below the metal sieve mesh passes through the metal sieve mesh or punching metal, preferably the punching metal, packed (loaded) with the tapping material, and may be supplied to the subsequent step (see FIG. 2).

In the sieve classifying apparatus illustrated in FIG. 2, a punching metal 24 is disposed below each of three metal sieve meshes 21 to 23 having different mesh opening sizes, and tapping balls 25 are packed on this punching metal 24. The mesh opening sizes of the three metal sieve meshes 21 to 23 decrease stage by stage from top to bottom, and for instance, the mesh opening sizes of the three metal sieve meshes 21, 22 and 23 are 1,000 μm, 850 μm, and 100 μm, respectively.

Here, since the metal sieve mesh or punching metal packed (loaded) with the tapping material is installed below the metal sieve mesh used for the classification of the water absorbent resin, it is preferable that the shape be substantially the same as that of the metal sieve mesh. For example, when the metal sieve used for the classification of the water absorbent resin is circular in shape, it is preferable that the metal sieve mesh or punching metal packed (loaded) with the tapping material be similarly circular in shape.

The hole diameter of the punching metal described above is smaller than the tapping material, and is desirably 5 mm or greater, and more preferably 10 mm or greater. Meanwhile, there are no particular limitations on the upper limit of the hole diameter of the punching metal, but the hole diameter is preferably 30 mm or less. Furthermore, from the viewpoint of classification efficiency, it is preferable that the punching metal have a hole diameter that is 5 times or more the mesh opening size of a metal sieve mesh. More preferably, the punching metal has a hole diameter that is from 6 times to 20 times the mesh opening size of a metal sieve mesh.

The hole ratio of the punching metal is preferably 15% to 50%, more preferably 20% to 45%, and still more preferably 25% to 40%. Meanwhile, the hole ratio is defined by the hole, pitch (P) and the like, but in the case where there are no holes in certain regions, for example, in the case where the punching metal has a rim, the hole ratio of the punching metal is defined as an area which also includes that regions. When the hole ratio is not in the range described above, there is a tendency that the physical property of the water absorbent resin deteriorate and the classification efficiency also decreases.

Furthermore, the distance (interval) between the sieve disposed above and the metal mesh (punching metal) installed below may be appropriately determined; however, in view of the effects of the present invention, the distance is usually preferably 1.1 to 5 times, more preferably 1.2 to 3 times, and still more preferably 1.3 to 2 times, relative to the diameter of the tapping material. If the interval described above is not in this range, there is a tendency that the physical property of the water absorbent resin obtained deteriorate and the classification efficiency decreases, which is not preferable.

Furthermore, in the present invention, the tapping material is provided on a punching metal that is disposed below a metal sieve mesh, but it is preferable that the tapping material be provided over the entire area of a punching metal in the plane direction, or on a punching metal that is divided into plural compartments (see FIG. 3).

Figure 3:
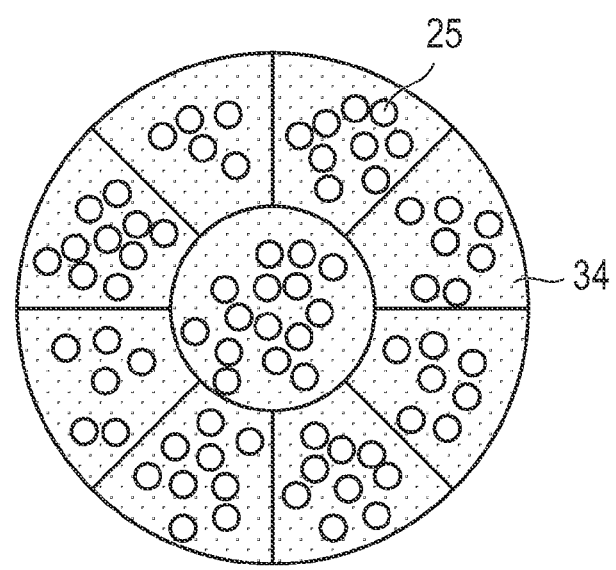
FIG. 3 is a schematic cross-sectional diagram, viewed from above, of tapping balls provided on a punching metal that is divided into plural compartments.

As illustrated in FIG. 3, when a punching metal divided into plural compartments (segmented screens) is used, the method of dividing the sections may be appropriately determined and is not particularly limited. However, for example, in the case of a circular punching metal, the punching metal may be segmented into two sections, four sections or eight sections, or the center area may be further divided into a circular region. The punching metal may also be segmented into 2 to 100 sections, preferably 4 to 50 sections, or more preferably 8 to 40 sections, by combining the ways to divide the punching metal. Meanwhile, the size or shape of each room, and the tapping material provided in each room may all be identical or may be different.

The tapping material (ball) described above is preferably used in combination with the tension of the constitution (i) described above. Further, preferably, the tapping material is used in further combination with the constitution s (iv) and/or (v) described below.

In the present invention, it is preferable that the tapping material be heated at the time of classification, from the viewpoints of an enhancement of the physical property of the water absorbent resin obtained and an enhancement of productivity. The heating temperature is preferably 40° C. or higher, more preferably 50° C. or higher, and still more preferably 60° C. or higher. The upper limit of the heating temperature is appropriately set, but there is a risk that excessive heating may reduce the effect of the tapping material, and the service life of the tapping material may be shortened. Therefore, the heating temperature is usually preferably 150° C. or lower, more preferably 120° C. or lower, still more preferably 100° C. or lower, particularly preferably 90° C. or lower, and most preferably 80° C. or lower. Accordingly, the temperature of the tapping material may be selected to be, for example, 40° C. to 100° C., 50° C. to 100° C., 60° C. to 100° C., or the like. However, the temperature is not intended to be limited to this range, and is defined to be in any arbitrary range selected from the upper limit value and the lower limit value of the heating temperature described above.

In order to heat the tapping material according to the present invention to the temperature range described above, the tapping material may be heated from an external source. As the heat source, the interior of the sieve, the surface of the sieve, and the water absorbent resin may be heated to a predetermined temperature, and the contact time or the amount of contact with the tapping material (for example, the flow rate of hot air to the sieve, the flow rate or retention rate of the water absorbent resin on the sieve, or the like) may be controlled.

In the present invention, since the tapping material wears out as the operating time elapses, it is preferable to regularly replace the tapping material depending on the wear of the tapping material. The wear of the tapping material can be monitored by means of, for example, the decrement of the diameter of the sphere, and the tapping material may be replaced at the time point when the decrement of the diameter reaches 3% or more, preferably 5% or more, more preferably 10% or more, and still more preferably 20% or more. If the tapping material is not regularly replaced, the physical properties of the water absorbent resin may gradually deteriorate with the lapse of the operating time. Further, the time (period) for replacement may be appropriately determined, but the tapping material may be replaced preferably after a substantially continuous operation for 30 days to 2 years, and more preferably 60 days to one year. Meanwhile, the term "substantially continuous operation" means a state in which, even in the case of including some resting or conversion periods, continuous operation is carried out for 80% or more, 90% or more, or 95% or more, of the operating period.

(iv) Classification Aid Particle

In the classification step of the present invention, a classification aid particle other than the water absorbent resin may also be used. That is, in the classification step that is carried out before the surface crosslinking step and/or after the surface crosslinking step, the water absorbent resin powder and a classification aid particle may be introduced to the metal sieve mesh used in the classification step. Preferably, from the viewpoints of the classification efficiency and the physical property of the water absorbent resin, the water absorbent resin powder and a classification aid particle having a specific gravity different from that of the water absorbent resin powder are introduced to the metal sieve mesh used in the classification step, and a fine powder of the water absorbent resin and the classification aid particle are removed. There are no particular limitations on the classification aid particles, but an inorganic fine particle or an organic fine particle, which has a larger specific gravity as compared with the water absorbent resin powder, may be used. Preferably, an inorganic fine particle, and more preferably, a water-insoluble inorganic fine particle is used. At the time of classifying the water absorbent resin powder, the classification aid particle is mixed therewith, and after classification, particularly after sieve classification, fine particles of the water absorbent resin and the classification aid particle are removed in a mixed state. The classified water absorbent resin fine particles and the classification aid fine particles can be optionally separated, and then reused.

The classification aid particle used in the present invention is such that particle having a specific gravity larger than the specific gravity of the water absorbent resin powder (in the case of sodium polyacrylate, about 1.6 $[g/cm^3]$), and usually, classification aid particle having a specific gravity of 2 $[g/cm^3]$ or greater, more preferably 2.0 to 4.0 $[g/cm^3]$, still more preferably 2.3 to 3.5 $[g/cm^3]$, and particularly preferably 2.5 to 3.0 $[g/cm^3]$, is used. Furthermore, the apparent specific gravity (volume specific gravity) thereof is preferably 0.5 $[g/cm^3]$ or greater.

The inorganic fine particle used, particularly water-insoluble fine particle, is preferably a powder of a water-insoluble polyvalent metal salt or a hydroxide or oxide thereof, and more preferably a powder of a water-insoluble polyvalent metal salt. Examples include calcium salts and aluminum salts, and calcium carbonate (2.711 $[g/cm^3]$) (calcite), 2.93 $[g/cm^3]$), calcium sulfate (2.96 $[g/cm^3]$ (anhydride), 2.32 $[g/cm^3]$ (dihydrate)), calcium oxide (3.35 $[g/cm^3]$) and the like are used. For example, calcium carbonate produced by pulverizing limestone is referred to as heavy calcium carbonate, and can be graded on the basis of the size of the particles. If necessary, calcium carbonate may be surface treated. There are no particular limitations on the organic fine particle, but examples include fluororesins and the like.

The particle size of the classification aid particle is preferably 100 μm or less, more preferably 10 μm or less, and still more preferably 1 μm or less. The lower limit is preferably 10 nm or greater, and still more preferably 50 nm or greater. The surface of the classification aid particle may be coated with a substance such as a fatty acid, rosin acid, lignin acid, or a quaternary ammonium salt, and the use amount of these substances is preferably 0.01% to 100% by weight, more preferably 0.1% to 10% by weight, and still more preferably 0.5% to 5% by weight, relative to the classification aid particles. Meanwhile, for the purpose of enhancing the anti-caking property, liquid permeability and diffusibility, methods of mixing a water absorbent resin with inorganic fine particles of silica, kaolin or the like (WO 92/18171 A, EP 629411 A, U.S. Pat. No. 6,124,391, JP 59-80459 A, and the like) are known. However, according to the present invention, the classification aid particle (preferably, 10% by weight or more of the classification aid particles added, and preferably, in sequence, 30% by weight or more, 50% by weight or more, 70% by weight or more, and particularly preferably 90% by weight or more) is removed together with fine particles of the water absorbent resin, for the purpose of enhancing the classification efficiency of the water absorbent resin powder or enhancing liquid permeability of the water absorbent resin obtained. Meanwhile, the proportion of the classification aid in the mixture of the classification aid particle and the water absorbent resin fine particle is measured by appropriately employing a measurement method depending on the classification aid particles used.

The classification aid particle of the present invention is preferably used in the classification step before and/or after surface crosslinking, and more preferably after surface crosslinking. Further, the classification aid particle is preferably used at the time of classification of fine powder in particular, as in the case of the (c) airbrush described above, and it is preferable that the classification aid particle be added over a sieve having a mesh opening size of 200 μm or less, and more preferably a sieve having a mesh opening size of 150 μm or less. The lower limit of the mesh opening size of the sieve described above is preferably 30 μm or larger, more preferably 45 μm or larger, and still more preferably 75 μm or larger. The classification aid particle is preferably used for the classification of fine powders of a water absorbent resin of a specific range, so as to promote an enhancement of liquid permeability (SFC or GBP).

The classification aid particle described above is preferably used in combination with the (i) tension described above. It also may be used in combination with any one of the (ii) airbrush below the sieve and the (iii) tapping material below the sieve.

(v) Damage Monitoring of Classifying Mesh

In the present invention, it is preferable to perform classification while the presence or absence of damage to the classifying mesh (metal sieve mesh) is steadily monitored. That is, according to the present invention, it is preferable to monitor the presence or absence of damage to the metal sieve mesh used in the classification step, in the classification steps that are carried out before the surface crosslinking step and after the surface crosslinking step. By steadily monitoring damage of the sieve mesh, any deterioration of the physical property can be instantly checked, and substandard products can be suppressed to a minimum level even in huge scale production. There are no particular limitations on the method of checking damage of the classifying mesh, but examples of the means for detecting destruction of the classifying mesh include methods of electrically detecting destruction by using ultrasonic waves or high frequency waves (for example, WO 2004/045198 A, JP 11-290781 A, or the like); and methods of detecting changes in the electrostatic capacity (for example, JP 04-281882 A). Furthermore, as an example of a suitable mesh destruction detecting system, also available is a method of attaching a Centriscan™ (Nishimura Machine Works Co., Ltd.), which automatically senses damage (breakage) of the classifying mesh by using microwaves, to a circular sieve machine that has been heated or kept warm.

A suitable method of using ultrasonic waves may be a non-destructive inspection method, and specific examples thereof include an AE (acoustic emission) method and an ultrasonic flaw detection method. The ultrasonic flaw detection method is a method of analyzing a signal produced by ultrasonic waves that have been transmitted and reflected by defects.

Conventionally, damage to the sieve mesh has been detected based on the changes in the particle size of the water absorbent resin. However, in huge scale production (particularly, continuous production at a rate of 1 [t/hr] or more), a significant change in the particle size distribution is detected, and there was even an occurrence in which a large quantity of substandard products were produced without recognizing damage to the sieve mesh. Examples of the conventional method described above include a detection method disclosed in WO 2008/037674 A, which is based on a method of irradiating electromagnetic waves to the mass flow rate of a carrier that flows at a rate of at least 0.1 [m/s].

On the contrary to this conventional detection method, in the present invention, damage to the sieve mesh can be instantly determined by directly inspecting the damage to the sieve mesh by ultrasonic waves or high frequency waves, and particularly by an acoustic emission (AE) method, and as a result, stable continuous production is enabled. The damage monitoring is preferably used in combination with the tension of the constitution (i) described above, and can be used in further combination with any one of the (ii) airbrush below the sieve and the (iii) tapping material below the sieve.

(AE Method; Acoustic Emission Method)

The AE method is capable of detection of the initial signs of crack generation, and may also be used for the monitoring of crack generation during operation or for the monitoring of the progress of cracks. The AE (acoustic emission) waves are detected by using an AE sensor that is attached directly to a propagation medium. Inside the sensor, a piezoelectric element is fixed so as to convert the AE waves that have arrived to an electric signal. This signal is amplified by about 40 dB (100 times) at a built-in amplifier in order to improve the S/N (signal/noise) ratio, and is further amplified, optionally, by about 20 dB (10 times) at an externally attached amplifier. Subsequently, the amplified signal is inputted to the AE measuring apparatus to be analyzed.

AE (acoustic emission) is defined as a "phenomenon in which when a material is deformed or cracks are generated, the material emits the strain energy accumulated within the material, as an elastic wave." A method of evaluating the course of destruction of a material by detecting this elastic wave with a transducer, that is, an AE sensor, installed at the surface of the material, and carrying out signal processing, is an AE method. The AE signal that is detected is usually in a frequency range of several kHz to several MHz. For example, in metal materials, the AE generated therefrom frequently transmit signals having components in the frequency region of mainly 100 kHz to 1,000 kHz.

The AE sensor that is used to detect signals, is generally equipped with a piezoelectric element such as PZT (lead zirconate titanate) and is closely attached to the material surface by means of an adhesive or an acoustic coupler such as a silicone grease, to thereby detect AE signals. The acoustic emission (AE) signals can be categorized as a burst type waveform, and the observed AE signals can be categorized into two kinds having different properties. One of them is an AE waveform that is called burst type, in which the waveform has a sharp rise and is attenuated, and the other is a continuous AE waveform with a relatively high frequency. Since the burst type AE waveform is transmitted as a result of crack propagation or transformation occurring mainly in solids, the burst type AE waveform is detected in accordance with the progress of destruction.

(c) Place of Classification Step

The classification step of the present invention is provided before and/or after the surface crosslinking step, and preferably, the classification step is carried out before and after the surface crosslinking step. Furthermore, it is preferable that the classification step be provided in least two places after the surface crosslinking step, and more preferably, the classification step is provided in two or more places after the surface crosslinking step and is also provided in one or more places before the surface crosslinking step. Particularly, preferably, the classification step is provided in two or more places after the surface crosslinking step and also in two or more places before the surface crosslinking step. When the classification step is provided in two or more places, particularly in two places, after surface crosslinking, classification is first carried out after surface crosslinking, subsequently classification of fine powder (particularly, a fine powder having a particle size of 200 µm or less, more preferably particles having a size of 150 µm or less, and still more preferably 80 µm to 120 µm) is carried out as a final step, and immediately after that, the powder is stored in a product hopper (final hopper). That is, according to the preferred embodiment, the classification step is carried out as a final step immediately before the product is stored in a product hopper. It is preferable because this operation allows a reduction in the fine powder or powder dust, and an enhancement of liquid permeability (GBP or SFC).

Furthermore, when the distance of transport (for example, pneumatic transport) from the classification step to the subsequent step is long, it is not preferable because fine powder or powder dust may be generated again by damage to the product during transport. Therefore, the distance from the final classification step, particularly the fine powder classification, to the product hopper is preferably set to 0 m to 100 m or less, and preferably, in the following sequence, 50 m or less, 25 m or less, 10 m or less, and 5 m or less.

(d) Removal of Electricity in Classification

In the present invention, it is preferable to implement removal of electricity in at least one or more of the classification steps of the constitutions (i) to (v) described above (preferably, the sieve classification step). When removal of electricity is achieved in the classification steps, the physical property of the surface crosslinked water absorbent resin, particularly liquid permeability (for example, SFC), is improved. Such an effect is markedly exhibited in the production of a water absorbent resin having high liquid permeability or industrial continuous production, particularly when a water absorbent resin having an SFC of $10[\times 10^{-7} \text{ cm}^3 \cdot \text{s} \cdot \text{g}^{-1}]$ or more is produced or continuous production at a rate of 1 [t/hr] or more is continued for 24 hours or longer, rather than small scale production at a laboratory level. Classification by removal of electricity is described in Patent Literature 30 described above (WO 2010/032694 A).

(Method for Removal of Electricity)

In the present invention, removal of electricity may be carried out for at least one of the "classifying apparatus", the "water absorbent resin powder" and the "sieve." Since these three are brought into contact with each other in a classification step, any one of them may be removed of electricity. It is preferable to remove of electricity of the classifying apparatus and/or the sieve itself.

As the removal of electricity method, for example, the following methods (A) to (C) can be applied, but the present invention is not intended to be limited to these.

(A) Removing of electricity brush: removal of electricity from the sieve surface where static electricity has been generated.

(B) Ionized gas stream (ion generating brush): removal of electricity by applying a high voltage and thereby generating ions.

(C) Ground connection (earth): removal of electricity of static electricity generated in a rotating object, a rotating shaft, a rotating body and an apparatus In the case of using a removing of electricity brush of the item (A) described above, a self-discharge method of providing a small gap between the removing of electricity brush and a charged object may be employed, or a ground leakage method of removing electric charge by bringing a grounded (earthed) removing of electricity brush into contact with a charged object, and removing the accumulated static electricity as a leak current may also be employed. As specific examples of such a removing of electricity brush, brushes produced from a stainless steel fiber, a carbon fiber, an amorphous fiber, a chemical fiber, a plant fiber, animal hair, and the like are preferred, and the wire diameter is usually preferably 1 µm to 100 µm, and more preferably 5 µm to 20 µm. Further, the wire length is usually preferably 1 mm to 100 mm, and stainless steel extra-fine processing is more preferred.

In the case of using the ionized gas stream (ion generating brush) of the item (B) described above, an example of the ion generating brush that can be used includes a static eliminator (ionizer). In such a removal of electricity method, ions are produced in air or in another gas, and the electrification charge is neutralized by these ions. For that reason, a removing of electricity apparatus is also called an ionizer. Specifically, the amount of electric charge and the electrification charge of a classifying apparatus or a water absorbent resin may be measured by using a static eliminator (ionizer), and an electrically neutral state may be attained by applying an opposite charge to the plus (+) charge or the negative (−) charge. At this time, a balance may be achieved between the optimal removal of electricity in accordance with the condition of electrification of a charged object and the control of ion balance. The amount of electric charge of the charged object may be determined by measuring the ion current by using an ion current detection circuit mounted in the controller. As such, the method (B) of completely deactivating static electricity by neutralizing the charge with a charge of reverse polarity is a preferred method for water absorbent resins.

In the case of using the ground connection of the item (C) described above, a method of removing of electricity by electrically connecting a building or a stand, on which the classifying apparatus is installed, to an earth with the ground resistance value described below, bringing a charged object into contact with the apparatus, and removing the accumulated static electricity as a leak current, may be used. This method is simple and easy, and is highly effective because the classifying apparatus as a whole works as a removing of electricity apparatus. Thus, it is one of the preferred methods for water absorbent resins.

The leak current removed at the time of such removal of electricity preferably flows to the ground through the ground connection (earth) with a ground resistance value described below. That is, in the classification step of the present invention, it is preferable that removal of electricity be achieved by using a ground connection with a ground resistance value described below.

(Ground Resistance)

Ground resistance means a resistance value against a current that flows from an earth electrode buried in the soil for a ground connection to the ground. As the measurement method, measurement may be made by using a commercially available ground resistance meter. A preferred range of the ground resistance value is preferably 100Ω or less, more preferably 10Ω or less, and still more preferably 5Ω or less, from the viewpoint of the classification step. There are no particular limitations on the lower limit of the ground resistance value, and a smaller value is more preferred. However, the ground resistance value is usually 1Ω or greater.

(e) Classifying Apparatus

The present invention is preferably constituted such that the classifying apparatuses described below are further used in at least one or more classification steps (preferably, sieve classification steps) of the constitutions (i) to (v) described above.

(Classifying Mesh)

In the present invention, a water absorbent resin powder is classified by using a classifying mesh. Examples of the classifying mesh include various standard sieves of JIS, ASTM and TYLER. These sieves may be plate sieves or may be mesh sieves. The shape of the mesh sieve is appropriately selected by making reference to JIS Z8801-1 (2000) or the like. The mesh opening size of the standard sieves is preferably in the range of 10 µm to 100 mm, and still more preferably in the range of 20 µm to 10 mm, and it is preferable to use one kind or two or more kinds of sieves, particularly metal sieves.

Furthermore, the area of the sieve mesh (area of the sieve mesh surface) is preferably 1 to 10 $m^2$/sheet, and more preferably 1.5 to 7 $m^2$/sheet, from the viewpoint of classification efficiency.

The sieve classification may be carried out such that only the upper part may be classified, or only the lower part may be classified. Preferably, however, it is preferable to classify the upper limit and the lower limit simultaneously. That is, it is preferable to simultaneously use plural sieves, and still more preferably, sieves of at least three kinds of mesh opening sizes are used in view of physical property improvement. As such a method, it is preferable to use intermediate sieves or upper sieves, in addition to the predetermined sieves of the upper position and the lower position. A suitable sieve is, for example, a sieve having a mesh opening size of 850 µm to 1,000 µm, 710 µm to 850 µm, or 600 µm to 710 µm, as the upper limit, and a sieve having a mesh opening size of 150 µm to 225 µm as the lower limit. Still more preferably, sieves may be appropriately added in the middle or in the upper part.

(Classifying Apparatus)

The classifying apparatus used in the present invention is not particularly limited as long as it has a sieve mesh surface, and examples include apparatuses that are categorized into vibrating screens and sifters. Examples of the vibrating screens include a tilted type, a Low-head type, Hum-mer, Rhewum, Ty-Rock, Gyrex, Eliptex, and the like, and examples of the sifters include a reciprocating type, Exolon-grader, Traversator-sieb, Sauer-meyer, Gyratory, Gyrosifter, Ro-tex, and the like. These are minutely categorized based on the shape of motion of the mesh surface (circular, elliptical, linear, arc, para-oval, spiral, or helical), mode of vibration (free vibration or forced vibration), driving method (eccentric shaft, unbalanced weight, electromagnetic, or impact), tilt of the mesh surface (horizontal or tilted), method of installation (floor type or suspended type), or the like. Among them, it is preferable that the metal sieve mesh trace a three-dimensional motion trajectory composed of eccentric tilt, radial tilt (tilt of the sieve mesh that disperses the material from the center to the periphery) or tangential tilt (tilt of the sieve mesh that controls the discharge speed over the mesh).

Particularly, in view of the effect of the present invention, a classifying apparatus which moves the sieve mesh surface in a helical form by the combination of radial tilt or tangential tilt, such as an oscillatory type apparatus (tumbler-screening machine), is preferred.

(Classification vibration)

There are no limitations on the sieve classifying apparatus that is appropriate for the classification method according to the present invention; however, preferably, it is preferable to use a plane classification method, and a tumble type sieve classifying apparatus is particularly preferred. This sieve classifying apparatus is typically vibrated in order to support classification. The vibration is preferably carried out to the extent that the product to be classified is guided to a spiral form (helical form) on the sieve. Such forcible vibration typically has an amplitude of vibration of 0.7 mm to 40 mm, and preferably 1.5 mm to 25 mm, and a frequency of vibration of 60 rpm to 6,000 rpm, and preferably 100 rpm to 600 rpm.

(Guide)

In the present invention, it is also preferable that the sieve of the classifying apparatus have a guide for the water absorbent resin powder. By installing such a guide, classification can be carried out more efficiently. Such a guide apparatus has a function of guiding a water absorbent resin powder to the center of the sieve or the like, and the length is determined to be about 5% to 40% of the diameter.

(Material and Surface Roughness)

The material of the sieve apparatus is not particularly limited, and is appropriately selected from resins, metals and the like. However, a metallic sieve, where a contact surface with the water absorbent resin is also metallic, is preferred, and a stainless steel sieve is particularly preferred, as compared with a resin-coated sieve mentioned as an example in JP 11-156299 A. In this case, the effect of the present invention is more effectively exhibited. When stainless steel is mirror-surface finished, the physical property is even further improved. Examples of stainless steel include SUS304, SUS316, SUS316L, and the like. Magnestain is also suitably used.

From the viewpoint of an enhancement of the physical property, the adhesion of water absorbent resin fine particles to the inner surfaces of the sieve apparatus, and the like, it is preferable that the inner surface of the sieve apparatus (metal sieve mesh) used in the classification step in the present invention have the surface roughness (Rz) defined by JIS B 0601-2001 controlled to be 800 nm or less. That is, preferably, the material of the metal sieve mesh is SUS304 or SUS316, and the surface roughness (Rz) of the inner surface of the metal sieve mesh is 800 nm or less. The inner surface is flattened to have a surface roughness (Rz) of preferably 150 nm or less, still more preferably 100 nm or less, and particularly preferably 50 nm or less. Meanwhile, the surface roughness (Rz) means the maximum value of the maximum height (μm) of the surface asperity. The lower limit of the surface roughness (Rz) is 0 nm, but there is no big difference even at about 10 nm, and it is still sufficient even with a surface roughness of 10 nm or 20 nm. Another surface roughness (Ra) is also defined by JIS B 0601-2001. Ra is preferably 100 nm or less, more preferably 50 nm or less, and particularly preferably 5 nm or less. The lower limit of the surface roughness (Ra) is 0 nm, but there is no big difference even at about 1 nm. Such surface roughness can be measured with a probe type surface roughness meter according to JIS B 0651-2001. Further, such surface roughness can be measured with a light wave interference type surface roughness meter according to JIS B 0652-2002.

(f) Conditions for Classification

The present invention is preferably achieved under the conditions described below in at least one or more classification steps (preferably, sieve classifying steps) of the constitutions (i) to (v) described above, and particularly preferably, the sieves are heated or kept warm to a predetermined temperature. Furthermore, preferably, the conditions for classification include reduced pressure and ventilation of an gas stream.

(Heating Temperature)

According to the present invention, preferably, a classifying apparatus is used in a heated state and/or in a heat-retained state, in addition to removal of electricity. Furthermore, preferably, the water absorbent resin is also used in a state of being heated to a predetermined temperature.

Heating in the present invention refers to active provision of heat. Therefore, a heated state includes a case in which the classifying apparatus is heated to increase the temperature to a certain temperature in the early phase, and then heat is no longer supplied; a case in which heat is supplied to the classifying apparatus not only in the early phase but also steadily, and the like. Meanwhile, keeping warm means making it difficult to liberate heat without supplying heat, that is, making it difficult for the temperature to decrease.

In order to bring a classifying apparatus to a heated state and/or a heat-retained state, the temperature of the atmosphere in which the classifying apparatus is placed may be increased, or the like. A preferred classifying apparatus is a dry classifying apparatus equipped with a heating unit and/or a heat retention unit.

Such a classifying apparatus (temperature of the sieve used) is preferably used at a temperature in the range of 40° C. or higher, or further 40° C. to 80° C. More preferably, the classifying apparatus is used at a temperature in the range of 45° C. to 60° C. When the temperature is 40° C. or higher, deterioration of the physical property is prevented, and when the temperature is lower than 100° C. or 80° C., the economic inefficiency caused by high temperature can be prevented, and the adverse effect on the classification efficiency can be prevented.

It is preferable that the classifying apparatus be used at a temperature that is not lower by 20° C., and more preferably not lower by 10° C., than the temperature of the water absorbent resin powder.

Furthermore, when a water absorbent resin powder is handled, the water absorbent resin powder introduced to the classification step is brought to a temperature equal to or higher than room temperature, and preferably 40° C. or higher. For example, it is preferable to heat the water absorbent resin powder to 40° C. to 100° C., and more preferably to 50° C. to 80° C. In order to obtain a water absorbent resin at such a temperature, the water absorbent resin may be appropriately heated, or a water absorbent resin obtained after the heating at the drying step or the surface crosslinking step may be kept warm.

(Reduced Pressure)

It is preferable to carryout the classification step under reduced pressure in order to enhance the physical property after surface crosslinking. The term "reduced pressure" means a state in which the air pressure is lower than the atmospheric pressure, and the pressure difference between the air pressure and the atmospheric pressure is expressed as a positive (plus) value. For example, when the atmospheric pressure is standard atmospheric pressure (101.3 kPa), the phrase "the degree of pressure reduction is 10 kPa," means that the air pressure is 91.3 kPa.

According to the present invention, from the viewpoint of classification efficiency, the lower limit of the degree of pressure reduction is preferably greater than 0 kPa, more preferably 0.01 kPa or greater, and still more preferably 0.05 kPa or greater. Furthermore, from the viewpoint of suppressing uplift of the powder in the system and lowering the cost for the exhaust apparatus, the upper limit of the degree of pressure reduction is preferably 10 kPa or less, more preferably 8 kPa or less, still more preferably 5 kPa or less, and particularly preferably 2 kPa or less. A preferred value range of the degree of pressure reduction can be arbitrarily selected to be between the lower limit and the upper limit described above.

(Gas Stream)

In the classification step, it is preferable that a gas stream passes through, and preferably, a gas stream, and particularly preferably air is passed through over the water absorbent resin powder. Preferably, countercurrent gas streams are ventilated above and below the sieve mesh (metal sieve mesh). The amount of this gas is typically 0.1 to 10 [m$^3$/hr], preferably 0.5 to 5 [m$^3$/hr], and particularly preferably 1 to 3 [m$^3$/hr], per 1 m$^2$ of the sieve area, and at that time, the gas volume is measured under standard conditions (for example, under the conditions of 25° C. and 1 bar). Particularly preferably, the gas stream is heated, before being introduced into the sieve classifying apparatus, typically to 40° C. or higher, preferably 50° C. or higher, more preferably 60° C. or higher, still more preferably 65° C. or higher, and particularly preferably 70° C. or higher. The temperature of the gas stream is usually 120° C. or lower, preferably 110° C. or lower, more preferably 100° C. or lower, still more preferably 90° C. or lower, and particularly preferably 80° C. or lower.

The dew point of the gas stream is preferably 15° C. or lower, and more preferably 10° C. or lower. There are no particular limitations on the lower limit of the dew point, but in consideration of cost performance, the lower limit of the dew point is preferably −10° C. or higher, and more preferably about −5° C.

(Atmospheric Dew Point)

The dew point of the atmosphere (air) in which the classification step is carried out is preferably 15° C. or lower, more preferably 10° C. or lower, still more preferably 5° C. or lower, and particularly preferably 0° C. or lower. There are no particular limitations on the lower limit of the dew point, but in consideration of cost performance, the lower limit of the dew point is preferably −10° C. or higher, and more preferably −5° C. or higher. Furthermore, the temperature of the gas is preferably 10° C. to 40° C., and more preferably 15° C. to 35° C.

As the method of controlling the dew point, the gas, preferably air, may be appropriately dried, and examples thereof include a method of using a membrane dryer, a method of using a cooling adsorption dryer, a method of using a diaphragm dryer, and methods of using these dryers in combination. In the case of using an adsorption dryer, the adsorption dryer may be a heating regeneration type, a non-heating regeneration type, or a non-regeneration type.

(Number of Apparatuses)

In the production method of the present invention, from the viewpoints of an enhancement and stabilization of the physical property of the water absorbent resin, the polymerization step is carried out by continuous belt polymerization or continuous kneader polymerization, and it is preferable that in a series of the polymerization steps, plural classification steps be carried out in parallel.

Here, the term "a series" in the present invention means one series where the steps are carried out from the stage of raw materials (monomers) to the stages of obtaining a water-containing gel-like crosslinked polymer, a water absorbent resin powder, a water absorbent resin, and a final product with progression of processes. When the system is branched into two systems, the case is called "two series". Therefore, the term "two or more series" refers to an embodiment in which in the same step, two or more apparatuses are disposed in parallel, and those apparatuses are operated simultaneously or alternately. Furthermore, without being limited to the classification step only, it is preferable that the pulverization step, the surface crosslinking step and the like coming after the drying step be carried out in two series. That is, in a series of the polymerization step described above, it is preferable that the classification step be carried out in two series, and it is most preferable that all the steps such as the pulverization step and the surface crosslinking step be carried out in two or more series.

(2-6) Surface Crosslinking Step

The present step is a step of crosslinking the vicinity of the surface of the water absorbent resin powder obtained in the pulverization step or the classification step described above by using a surface crosslinking agent (surface crosslinking reaction), for an enhancement of the absorption performance, and through the surface crosslinking, a water absorbent resin which undergoes less coloration and has a higher degree of whiteness is obtained.

There are no particular limitations on the surface crosslinking agent that can be used in the present invention, but various organic or inorganic surface crosslinking agents (ionic bonding surface crosslinking agents) may be used. Among them, organic surface crosslinking agents are preferred, and it is more preferable to use an organic surface crosslinking agent and an ionic bonding surface crosslinking agent (ionic crosslinking agent) in combination.

Specific examples of the organic surface crosslinking agents include polyhydric alcohol compounds, epoxy compounds, polyvalent amine compounds or condensates thereof with haloepoxy compounds, oxazoline compounds, (mono-, di- or poly-)oxazolidinone compounds, and alkylene carbonate compounds, and particularly, dehydration ester-reactive crosslinking agents containing polyhydric alcohol compounds, alkylene carbonate compounds and oxazolidinone compounds, which require reactions at high temperatures, can be used. More specifically, the compounds listed as examples in U.S. Pat. No. 6,228,930, U.S. Pat. No. 6,071,976, U.S. Pat. No. 6,254,990, and the like can be used. Examples include polyhydric alcohol compounds such as mono-, di-, tri-, tetra- or propylene glycol, 1,3-propanediol, glycerin, 1,4-butanediol, 1,3-butanediol, 1,5-pentanediol, 1,6-hexanediol, and sorbitol; epoxy compounds such as ethylene glycol diglycidyl ether and glycidol; alkylene carbonate compounds such as ethylene carbonate; oxetane compounds; and cyclic urea compounds such as 2-imidazolidinone and the like. The use amount of the organic surface crosslinking agent is appropriately determined in the range of preferably 0.001 parts to 10 parts by weight, and more preferably 0.01 parts to 5 parts by weight, relative to 100 parts by weight of the water absorbent resin powder.

Furthermore, it is preferable to use water as a solvent at the time of mixing the water absorbent resin and the surface crosslinking agent. The use amount of water described above is appropriately determined in the range of preferably 0.5 parts to 20 parts by weight, and more preferably 0.5 parts to 10 parts by weight, relative to 100 parts by weight of the water absorbent resin powder. Further, a hydrophilic organic solvent may be optionally used in combination, in addition to water. The use amount thereof is appropriately determined in the range of preferably 0 parts to 10 parts by weight, and more preferably 0 parts to 5 parts by weight, relative to 100 parts by weight of the water absorbent resin powder.

Furthermore, at the time of mixing a surface crosslinking agent solution, a water-insoluble fine particle powder (water-insoluble particle) or a surfactant may be incorporated to the extent that the effect of the present invention is not impaired. In regard to the type, use amount, or the like of the fine particle powder or the surfactant, examples are given in U.S. Pat. No. 7,473,739 and the like. However, the use amount is appropriately determined in the range of preferably 0 parts to 10 parts by weight, more preferably 0 parts to 5 parts by weight, and still more preferably 0 parts to 1 part by weight, relative to 100 parts by weight of the water absorbent resin powder.

In the present step, after the water absorbent resin powder and the surface crosslinking agent are mixed, the mixture is preferably subjected to heating treatment and subsequently to optionally cooling treatment. The heating temperature at the time of the heating treatment described above is preferably 70° C. to 300° C., more preferably 120° C. to 250° C., and still more preferably 150° C. to 250° C. If the treatment temperature described above is lower than 70° C., the heating treatment time increases, causing a decrease in productivity, and also a uniform surface crosslinked layer cannot be formed, which is not preferable. Furthermore, if the treatment temperature is higher than 300° C., the water absorbent resin powder is deteriorated, and it is not preferable. Furthermore, the heating time at the time of the heating treatment described above is preferably in the range of 1 minute to 2 hours. The heating treatment described above can be carried out in a conventional dryer or a conventional heating furnace. Meanwhile, the surface crosslinking methods disclosed in EP 0349240 A, EP 0605150 A, EP 0450923 A, EP 0812873 A, EP 0450924 A, EP 0668080 A, JP 7-242709 A, JP 7-224304 A, U.S. Pat. No. 5,409,771, U.S. Pat. No. 5,597,873, U.S. Pat. No. 5,385,983, U.S. Pat. No. 5,610,220, U.S. Pat. No. 5,633,316, U.S. Pat. No. 5,674,633, U.S. Pat. No. 5,462,972, WO 99/42494 A, WO 99/43720 A, WO 99/42496 A, and the like can be preferably applied to the present invention.

(Inorganic Surface Crosslinking Agent)

According to the present invention, an inorganic surface crosslinking agent (ionic bonding surface crosslinking agent) can be used other than the organic surface crosslinking agent described above, for the purpose of enhancing the physical property such as liquid permeability. There are no particular limitations on the inorganic surface crosslinking agent used, but examples include polyvalent metal salts (organic salts or inorganic salts) having a valence of 2 or higher, and preferably a valence of 3 or 4, or hydroxides. Specific examples of the polyvalent metals include aluminum, zirconium and the like, and aluminum lactate and aluminum sulfate are preferably used. The polyvalent metal salts are preferably used in a solution state, and are more preferably in the form of an aqueous solution, from the viewpoints of handleability and the miscibility with the water absorbent resin powder. The amount of addition of the inorganic surface crosslinking agent is such that the optimum amount may vary with the type or particle size of the water absorbent resin, but usually, the amount of addition is in the range of greater than 0 and equal to or less than 10 parts by weight, preferably 0.001 parts to 5 parts by weight, and still more preferably 0.002 parts to 3 parts by weight, relative to 100 parts by weight of the solid content of the water absorbent resin powder.

These inorganic surface crosslinking agents are used simultaneously with or separately from the organic surface crosslinking agents. Preferably, from the viewpoint of water absorption performance (particularly, high liquid permeability), it is preferable to add an inorganic surface crosslinking agent to the water absorbent resin powder after the surface crosslinking by means of an organic surface crosslinking agent (for example, at the time of a cooling treatment).

Meanwhile, surface crosslinking by means of polyvalent metals is described in WO 2008/09843, U.S. Pat. No. 7,157,141, U.S. Pat. No. 6,605,673, U.S. Pat. No. 6,620,889, US 2005/0288182 A, US 2005/0070671 A, US 2007/0106013 A, and US 2006/0073969 A, or the like.

(Cooling Treatment)

A cooling treatment is optionally carried out, for the purpose of stopping, controlling or the like the surface crosslinking reaction, before a water absorbent resin powder obtained by being heated in the surface crosslinking step to have the surface vicinity crosslinked is fed to a subsequent step (for example, a classification step (particle size regulation step)). There are no particular limitations on the cooling apparatus used in this cooling treatment, but for example, a paddle dryer; a biaxial stirred dryer in which cooling water is circulated in the inner wall and inside other heat transfer surfaces; a groove type stirred dryer; or the like can be used. The temperature of the water absorbent resin powder obtained after the cooling treatment can be adjusted to below the heating temperature, that is, equal to or higher than 25° C. and lower than 80° C., and preferably can be adjusted to equal to or higher than 30° C. and equal to or lower than 60° C. However, in the case of carrying out a classification step (particle size regulation step) after the cooling treatment, it is preferable to carry out a cooling treatment for the water absorbent resin powder such that the conditions described above in the section (f) Conditions for classification are satisfied.

Meanwhile, in the surface crosslinking step, there are occasions in which the surface crosslinking of a water absorbent resin powder is carried out at room temperature. In this case, since the water absorbent resin powder obtained by surface crosslinking is not heated, this cooling treatment may not be carried out.

Furthermore, for the purpose of enhancing the physical property such as liquid permeability, a polyamine polymer may also be used simultaneously or separately, other than the organic surface crosslinking agent and the inorganic surface crosslinking agent. The polyamine polymer is such that a polyamine polymer having a weight average molecular weight of about 5,000 to 1,000,000 is particularly preferred, and examples thereof are listed in U.S. Pat. No. 7,098,284, WO 2006/082188 A, WO 2006/082189 A, WO 2006/082197 A, WO 2006/111402 A, WO 2006/111403 A, and WO 2006/111404 A, and the like.

A water absorbent resin obtained by surface treating with the organic surface crosslinking agent, inorganic surface crosslinking agent and additive described above, preferably has at least one kind of a water-insoluble particle, a polyamine polymer and a polyvalent metal on the surface. A water absorbent resin in this form has excellent physical property (particularly, liquid permeability).

(2-7) Fine Powder Recycling Step (Fine Powder Collection Step and Granulation Step)

A fine powder recycling step according to the present invention is a process of separating a fine powder (particularly, a fine powder containing particles having a particle size of less than 150 μm as a main component, and particularly at a proportion of 70% by weight or more) obtained by drying and optionally by pulverizing and classifying, and then recycling the fine powder to the polymerization step or the drying step directly or after hydration of the fine powder. For example, the methods described in US 2006/247351 A, U.S. Pat. No. 6,228,930 and the like, can be applied. In the present invention, it is preferable to further include the fine powder recycling step after the classification step.

When a recycled fine powder is incorporated, the particle size can be controlled, and at the same time, a high solid content concentration, which is essential in the present invention, can be easily achieved by addition of the water absorbent resin powder. Furthermore, detachment of the water absorbent resin obtained after drying from the drying belt can be facilitated by the addition of a fine powder, and therefore, it is preferable.

(2-8) Deferrization Step

In the present invention, there are occasions in which metal wires are incorporated, such as in the case of using the removing of electricity brush described above, and thus, preferably a deferrization step, and more preferably a deferrization step using a magnet, is included after the classification step. When the deferrization step is carried out, metal components that are present in the water absorbent resin powder can be removed. A permanent magnet may be used for deferrization, and metal originating from a sieve, a brush, or the like may be removed by allowing a water absorbent resin powder that continuously flows, to pass through between magnets.

(2-9) Transport Step

In regard to the method of transporting a water absorbent resin before and after the classification step, and particularly preferably between the classification step and the surface crosslinking step, various methods can be used, but preferably, pneumatic transport is used. For the pneumatic transport, it is preferable to use dry air from the viewpoint that the excellent physical property of the water absorbent resin is stably retained. The upper limit of the dew point of the dry air is usually 20° C. or lower, preferably −5° C. or lower, more preferably −10° C. or lower, still more preferably −12° C. or lower, and particularly preferably −15° C. or lower. Furthermore, the lower limit of the dew point is usually −100° C. or higher, and preferably −70° C. or higher, and a dew point of about −50° C. is sufficient. Furthermore, the temperature of the dry air is preferably 10° C. to 40° C., and more preferably 15° C. to 35° C. The surface roughness (Rz) of the inner surface of the pneumatic transport pipe is in the same range as that of the surface roughness (Rz) of the inner surface of the sieve apparatus described above.

A heated gas (air) may also be used other than a dry gas (air). In this case, the heating method is not particularly limited, but the gas (air) may be directly heated by using a heat source, or the transport pipes or apparatuses are heated and thereby the gas (air) passing therethrough may be indirectly heated. The lower limit of the temperature of this heated gas (air) is preferably 20° C. or higher, and more preferably 30° C. or higher. Furthermore, the upper limit of the temperature of the heated gas (air) is preferably lower than 70° C., and more preferably lower than 50° C.

As the method of controlling the dew point, the gas (preferably, air) may be appropriately dried. Specific examples include a method of using a membrane dryer, a method of using a cooling adsorption dryer, a method of using a diaphragm dryer, and methods of using these dryers in combination. In the case of using an adsorption dryer, the adsorption dryer may be a heating regeneration type, or a non-heating regeneration type.

(2-10) Other Steps

In addition to the continuous steps described above, the fine powder recycling step described above, a granulation step, a fine powder removal step, and the like may be optionally provided. Furthermore, for the purpose of a color stability effect over time, prevention of gel deterioration, or the like, the additive described above may be optionally used, in some or all of the various steps described above. Furthermore, the production method of the present invention preferably includes a fine powder recycling step. Further, preferably, the production method further includes one or two or more steps such as a transport step, a storage step, a packing step, steps for adding other additive (a fine particle, a deodorizer, an antibacterial agent, and the like), and the like.

[3] PHYSICAL PROPERTIES OF WATER ABSORBENT RESIN

The water absorbent resin of the present invention contains a polyacrylic acid (salt)-type water absorbent resin as a main component, and is obtained by the polymerization method described above, surface crosslinking method or the like, when a use of the water absorbent resin in sanitary products, particularly paper diapers, is intended. Furthermore, for the water absorbent resin after the surface crosslinking step, it is preferable to control at least one or more physical properties among the various physical properties discussed in the following sections (3-1) to (3-7), and it is preferable to control two or more, particularly three or more, physical properties including the AAP. In the present invention, the term "water absorbent resin after the surface crosslinking step" means a water absorbent resin as a final product. For this reason, when a classification step is carried out after the surface crosslinking step, the water absorbent resin after the surface crosslinking step means a water absorbent resin as a final product after the classification step. When the water absorbent resin satisfies various physical properties such as described below, the water absorbent resin can exhibit sufficient performance even in high concentration diapers having a water absorbent resin concentration of 40% by weight or more.

(3-1) CRC (Absorption Capacity without Load)

The CRC (absorption capacity without load) of the water absorbent resin obtained by the present invention is preferably 10 [g/g] or greater, more preferably 20 [g/g] or greater, still more preferably 25 [g/g] or greater, and particularly preferably 27 [g/g] or greater. The upper limit of the CRC is not particularly limited, but the upper limit is preferably 50 [g/g] or less, more preferably 45 [g/g] or less, and still more preferably 40 [g/g] or less. If the CRC is less than 10 [g/g], the absorption amount of the water absorbent resin is low, and there is a risk that the water absorbent resin may not be suitable for the use in the absorbent materials in sanitary products such as paper diapers. Furthermore, if the CRC described above exceeds 50 [g/g], when such a water absorbent resin is used in absorbent materials, there is a risk that sanitary products having an excellent rate of liquid uptake may not be obtained, which is not preferable. Meanwhile, the CRC can be appropriately controlled by the internal crosslinking agent, surface crosslinking agent described above, or the like.

(3-2) AAP (Absorption Capacity Under Load)

As to the AAP (absorption capacity under load) of the water absorbent resin obtained by the present invention, for the purpose of prevention of leakage into paper diapers, which is achieved by the drying described above, the AAP under a pressure of 4.83 kPa (0.7 psi) is preferably 20 [g/g] or greater, more preferably 22 [g/g] or greater, and still more preferably 24 [g/g] or greater. The upper limit of the AAP is not particularly limited, but in view of the balance with other physical properties, the upper limit is preferably 40 [g/g] or less. When the AAP described above is less than 20 [g/g], if such a water absorbent resin is used in an absorbent material, there is a risk that a sanitary product which exhibits less return of liquid (usually, also referred to as "re-wet") when pressure is applied to the absorbent material, may not be obtained, and this is not preferable. Meanwhile, the AAP can be appropriately controlled by the surface crosslinking agent, particle size described above, or the like.

(3-3) SFC (Saline Flow Conductivity)

As to the SFC (saline flow conductivity) of the water absorbent resin obtained by the present invention, for the purpose of prevention of leakage into paper diapers, which is achieved by the drying described above, the SFC which is a liquid permeability characteristic of a liquid under pressure is preferably $1[\times 10^{-7} \text{ cm}^3 \cdot \text{s} \cdot \text{g}^{-1}]$ or greater, more preferably $10[\times 10^{-7} \text{ cm}^3 \cdot \text{s} \cdot \text{g}^{-1}]$ or greater, still more preferably $30[\times 10^{-7} \text{ cm}^3 \cdot \text{s} \cdot \text{g}^{1}]$ or greater, particularly preferably $70[\times 10^{-7} \text{ cm}^3 \cdot \text{s} \cdot \text{g}^{-1}]$ or greater, and most preferably $110[\times 10^{-7} \text{ cm}^3 \cdot \text{s} \cdot \text{g}^{-1}]$ or greater. The upper limit of the SFC is not particularly limited, but in view of the balance with other physical properties, the upper limit is preferably $3,000[\times 10^{-7} \text{ cm}^3 \cdot \text{s} \cdot \text{g}^{-1}]$ or less, and more preferably $2,000[\times 10^{-7} \text{ cm}^3 \cdot \text{s} \cdot \text{g}^{-1}]$ or less. When the SFC exceeds $3,000[\times 10^{-7} \text{ cm}^3 \cdot \text{s} \cdot \text{g}^{-1}]$ or greater, if such a water absorbent resin is used in an absorbent material, there is a risk that liquid leakage in the absorbent material may occur, and it is not preferable. Meanwhile, the SFC can be appropriately controlled by the drying method described above or the like.

(3-4) Ext (Extractables)

The Ext (extractables) of the water absorbent resin obtained by the present invention is preferably 35% by weight or less, more preferably 25% by weight or less, still more preferably 15% by weight or less, and particularly preferably 10% by weight or less. If the Ext is greater than 35% by weight, the gel strength of the water absorbent resin obtained is weak, and there is a risk that liquid permeability may deteriorate. Furthermore, when such a water absorbent resin is used in an absorbent material, there is a risk that a water absorbent resin which exhibits less return of liquid (re-wet) when pressure is applied to the absorbent material, may not be obtained, and this is not preferable. Meanwhile, the Ext can be appropriately controlled by the internal crosslinking agent described above or the like.

(3-5) Residual Monomers

The amount of residual monomers of the water absorbent resin obtained by the present invention is controlled, from the viewpoint of safety, preferably to 0 ppm to 500 ppm, more preferably 0 ppm to 400 ppm, still more preferably 0 ppm to 300 ppm, and particularly preferably 0 ppm to 200 ppm. Meanwhile, the amount of residual monomers can be appropriately controlled by the polymerization method described above or the like.

(3-6) Initial Color Tone

The water absorbent resin obtained by the present invention has excellent initial color tone. That is, the color tone of the water absorbent resin immediately after production (initial color tone), which may be obtained by the present invention, exhibits the following values. Meanwhile, the initial color tone refers to the color tone immediately after production, but is generally considered as the color tone measured before factory shipment. Furthermore, for example, if the water absorbent resin is stored in an atmosphere at below 30° C. and at a relative humidity of 50% RH, the initial color tone is the value measured within one year after production. Specifically, with respect to Hunter's Lab color scale, the L value (lightness) is preferably 85 or greater, more preferably 87 or greater, and still more preferably 89 or greater. Furthermore, the b value is preferably −5 to 10, more preferably −5 to 9, still more preferably −4 to 8, and particularly preferably −1 to 7. Further, the a value is −2 to 2, at least −1 to 1, preferably −0.5 to 1, and particularly preferably 0 to 1. Furthermore, in another color scale, the YI (yellow index) value is preferably 10 or less, more preferably 8 or less, and particularly preferably 6 or less. As another color scale, the WB (white balance) value is preferably 70 or greater, more preferably 75 or greater, and particularly preferably 77 or greater. The water absorbent resin obtained by the present invention is also excellent in coloration over time, and exhibits a sufficient degree of whiteness even in an acceleration test carried out under high temperature and high humidity. Meanwhile, the initial color tone and the coloration over time of the water absorbent resin of the present invention can be measured by the measurement method disclosed in WO 2009/005114 A.

(3-7) Moisture Content

The moisture content of the water absorbent resin obtained by the present invention is, from the viewpoint of the powder characteristics (prevention of static charge, impact resistant stability, and prevention of deterioration of physical properties during transport), preferably 0% to 15% by weight, more preferably 0% to 10% by weight, and still more preferably 0% to 3% by weight. Meanwhile, the lower limit of the moisture content is preferably 0.1% by weight or greater, more preferably 0.5% by weight or greater, still more preferably 1% by weight or greater, and particularly preferably 1.4% by weight or greater. The adjustment of the moisture content may be carried out by appropriately adjusting the heat treatment conditions at the time of the surface crosslinking step, or if necessary, the amount of addition of water.

Meanwhile, water in the water absorbent resin is an inhibitory factor at the time of classification; however, in the present invention, a water absorbent resin having the predetermined moisture content described above can be more effective in the classification step, than in an absolute dry state with a moisture content of less than 0.1% by weight. Therefore, the present invention can be preferably applied in the method for producing a water absorbent resin, which includes a classification step for the water absorbent resin having the moisture content described above.

[4] USE OF WATER ABSORBENT RESIN

The use of the water absorbent resin obtained by the production method according to the present invention is not particularly limited, and the water absorbent resin can be used in sanitary products such as paper diapers, sanitary napkins, and incontinence pads; and water absorbent articles such as agricultural and horticultural water retention agents, waste water solidifying agents, and industrial water stopping materials.

EXAMPLES

Hereinafter, the present invention will be described by way of Examples and Comparative Examples, but the present invention is not intended to be construed to be limited to these Examples. Furthermore, for convenience, the unit "liter" may be indicated as "L", and the unit "% by weight" as "wt %". Meanwhile, unless otherwise specified, the various physical properties described in the claims and Examples of the water absorbent resin obtained by the present invention were determined according to the EDANA methods and the Measurement Examples described below, under the conditions of room temperature (20° C. to 25° C.) and a humidity of 50 RH %.

1. Resin Solid Content (Solid Content)

In an aluminum cup in which the diameter of the bottom is about 50 mm, 1.00 g of a water absorbent resin was weighed, and the total weight W1 [g] of the sample (the water absorbent resin and the aluminum cup) was accurately weighed.

Subsequently, the sample was placed in an oven at an atmospheric temperature of 180° C., and thereby the water absorbent resin was dried. After a lapse of 3 hours, the sample was removed from the oven together with the aluminum cup and cooled to room temperature in a desiccator. Thereafter, the total weight W2 [g] of the dried sample (the water absorbent resin and the aluminum cup) was weighed, and the solid content (unit: [wt %]) was calculated according to the following formula:

Solid content [wt %]=100−{(W1−W2)/(weight of water absorbent resin [g])×100}   [Mathematical Formula 1]

Meanwhile, when the resin solid content of a particulate water-containing gel-like crosslinked polymer (particulate hydrogel), the measurement was made by changing the collection amount of the particulate hydrogel to 2 to 4 g, and the drying time to 24 hours.

2. SFC (Saline Flow Conductivity)

The SFC (saline flow conductivity) of the water absorbent resin obtained by the present invention was measured according to the descriptions of U.S. Pat. No. 5,669,894.

3. Other Physical Properties

The physical properties of the water absorbent resin obtained by the present invention such as the CRC (absorption capacity without load), the particle size distribution (see the section "PSD" described above: method described in ERT420.2-02), pH extractables (see the section "Ext" described above: method described in ERT470.2-02), and the amount of residual acrylic acid (see the section "Residual Monomers" described above: method described in ERT410.2-02) were measured according to the ERT of EDANA described above, or according to US 2006/204755 A.

Example 1

The following operation was carried out according to Example 1 of Patent Literature 30 (WO 2010/032694 A).

That is, as illustrated in FIG. 1, continuous production was achieved by using a continuous production facility for a water absorbent resin (production capacity: 1500 [kg/hr]), which includes a polymerization step (static polymerization on a belt), a gel grain refining (crushing) step, a drying step, a pulverization step, a classification step (classification step 1), a surface crosslinking step (a mixing step for a surface crosslinking agent, a heating step, and a cooling step), a particle size regulation step (classification step 2), a classification step 3, and transport steps that connect the respective steps. Meanwhile, the classification step 1, the surface crosslinking step, the classification step 2 and the classification step 3 described above were connected by pneumatic transport (dry air having a dew point of 10° C., or heated air at 60° C.)

Specifically, an aqueous solution (monomer concentration: 37 wt %) of a partial sodium salt of acrylic acid with a degree of neutralization of 75 mol %, containing 0.06 mol % (based on the monomer) of polyethylene glycol diacrylate (average n value (average degree of polymerization): 9) as an internal crosslinking agent, was used as an aqueous monomer solution (1), and the aqueous monomer solution (1) obtained was subjected to continuous feeding with a quantitative pump. Nitrogen gas was continuously blown into the middle of the transport pipe, and thus the oxygen concentration was adjusted to 0.5 [mg/L] or less.

Next, sodium persulfate/L-ascorbic acid were further continuously mixed by line mixing separately into the aqueous monomer solution (1) in amounts of 0.14 g/0.005 g (relative to 1 mole of the monomer), respectively. The mixture was supplied to a planar steel belt having weirs at both ends to form a layer having a thickness of about 30 mm, and static aqueous solution polymerization (continuous belt polymerization) was carried out continuously for 30 minutes at 95° C. (polymerization step).

A water-containing gel-like crosslinked polymer (1) (solid content concentration: 45 wt %) obtained by the polymerization step described above was finely divided to a size of about 1 mm by using a meat chopper having a hole diameter of 7 mm in an atmosphere at 60° C. (gel grain refining (crushing) step). Subsequently, the crosslinked polymer was loaded in a wide spread manner on a moving multi-hole plate of a continuously ventilated band dryer (dew point of hot air: 30° C.) to form a layer having a thickness of 50 mm, and was dried for 30 minutes at 185° C. Subsequently, the crosslinked polymer was cooled by being exposed to external air. Thus, a dry polymer (1) (solid content concentration: 96 wt %, temperature: 60° C.) was obtained (drying step).

The entire amount of the dry polymer (1) obtained was pulverized by continuously supplying the polymer to a three-stage roll mill (roll gaps: 1.0 mm/0.70 mm/0.50 mm from the top) (pulverization step), and then was classified by using an oscillatory type circular sieving apparatus (frequency of vibration: 230 rpm, radial tilt (gradient): 11 mm, tangential tilt (gradient): 11 mm, eccentricity: 35 mm, temperature of the apparatus: 60° C., dew point of the atmosphere in the apparatus: 13° C.) having a sieve diameter of 1,600 mm and metal sieve meshes having mesh opening sizes of 1,000 μm, 850 μm and 150 μm, respectively (material: SUS304, surface roughness of inner sieve surface Rz: 50 nm, surface roughness Ra: 4.8 nm, stretch tension: 50 [N/cm], area of sieve mesh: 2 [m²/sheet]). The particle fraction between the 850-μm metal sieve mesh and the 150-μm metal sieve mesh was collected, and thus a water absorbent resin powder (1) in which the proportion of particles having a particle size of 850 μm to 150 μm was about 98 wt % (CRC: 36 [g/g], solid content: 96 wt %, weight average particle size (D50): 450 μm, σζ: 0.35) was obtained. Meanwhile, the temperature of the water absorbent resin powder obtained after the pulverization step and supplied to the sieving apparatus, was maintained at 60° C. Furthermore, the stand on which this sieving apparatus was installed, was grounded with a ground resistance value of 5Ω (removal of electricity). Further, the degree of pressure reduction inside the sieving apparatus was adjusted to 0.11 kPa by an exhaust apparatus provided with a bag filter, and the sieving apparatus was ventilated with air having a dew point of 10° C. and a temperature of 60° C., at a rate of 2 [m³/hr] (classification step 1).

The water absorbent resin powder (1) obtained as described above was continuously supplied at a constant rate of 1,500 [kg/hr] to a high speed continuous mixer (Turbulizer, 1,000 rpm), and a surface treating agent solution consisting of a mixture liquid of 0.3 parts by weight of 1,4-butanediol, 0.5 parts by weight of propylene glycol, and 2.7 parts by weight of pure water, relative to 100 parts by weight of the water absorbent resin powder, was mixed with the powder by spraying. Subsequently, the mixture obtained was heat treated continuously for 40 minutes at 198° C. by using a paddle dryer (surface crosslinking step). Thereafter, the mixture was forcibly cooled to 60° C. by using the same paddle dryer (cooling step).

Furthermore, the 850-μm pass powder was classified by using the same oscillatory type circular sieving apparatus having a sieve diameter of 1,600 mm as the apparatus used in the classification step 1 described above (temperature of the apparatus: 60° C.; mesh opening size: 850 μm; stretch tension of the mesh: 50 [N/cm]; material: SUS316; dew point of the atmosphere inside the apparatus: 12° C.). The particles remaining on the sieve mesh having a mesh opening size of 850 μm were pulverized again, and then were mixed with the 850-μm pass powder. Thus, a particle size-regulated water absorbent resin (1) (moisture content: 1.5 wt %, extractables: 8.7 wt %, weight average particle size (D50): 445 μm, σζ: 0.39), in which the entire amount of the resin was a 850-μm pass powder, was obtained (particle size regulation step (classification step 2)). Meanwhile, the temperature of the water absorbent resin powder obtained after the pulverization step and supplied to the sieving apparatus, was maintained at 60° C. Furthermore, the stand on which this sieving apparatus was installed, was grounded (removal of electricity) with a ground resistance value of 5Ω. Further, the degree of pressure reduction inside the sieving apparatus was adjusted to 0.11 kPa by an exhaust apparatus provided with a bag filter, and the sieving apparatus was ventilated with air having a dew point of 10° C. and a temperature of 60° C., at a rate of 2 [m³/hr].

Subsequently, for the 850-μm pass powder obtained in the classification step 2 described above, fine powder having a particle size of less than 120 μm was removed by using the same oscillatory type circular sieving apparatus having a sieve diameter of 1,600 mm as the apparatus used in the classification step 1 described above (temperature of the apparatus: 60° C.; mesh opening size: 120 μm; stretch tension of the mesh: 50 [N/cm]; material: SUS316). Thus, a water absorbent resin (1) was obtained (classification step 3). Meanwhile, the temperature of the water absorbent resin powder obtained after the pulverization step and supplied to the sieving apparatus, was maintained at 60° C. Furthermore, the stand on which this sieving apparatus was installed, was grounded (removal of electricity) with a ground resistance value of 5Ω. Further, the degree of pressure reduction inside the sieving apparatus was adjusted to 0.11 kPa by an exhaust apparatus provided with a bag filter, and the sieving apparatus was ventilated with air having a dew point of 10° C. and a temperature of 60° C., at a rate of 2 [m³/hr].

While the water absorbent resin (1) obtained was continuously produced, sampling was carried out for every 1 ton, and a performance analysis was carried out for 20 tons of the water absorbent resin. The number of samples obtained was 20 samples, and the average CRC, AAP and SFC values were 30.3 [g/g] (CRC), 24.7 [g/g] (AAP), and $42[\times 10^{-7} \text{ cm}^3 \cdot \text{s} \cdot \text{g}^{-1}]$ (SFC), respectively. The details of the performance of the water absorbent resin (1) obtained are presented in Table 1. Meanwhile, even after a lapse of 365 days (12 months), there was neither a deterioration of physical properties nor a change in the particle size, and the apparatus operated stably.

Example 2

The same operation as that employed in Example 1 was carried out, except that the stretch tension (tension) of the metal sieve mesh of the classification step 3 used in Example 1 described above was changed to 40 [N/cm], and thus a water absorbent resin (2) was obtained.

While the water absorbent resin (2) obtained was continuously produced, sampling was carried out for every 1 ton, and a performance analysis was carried out for 20 tons of the water absorbent resin. The number of samples obtained was 20 samples, and the average CRC, AAP and SFC values were 30.2 [g/g] (CRC), 24.6 [g/g] (AAP), and $38[\times 10^{-7} \text{ cm}^3 \cdot \text{s} \cdot \text{g}^{-1}]$ (SFC), respectively. A slight decrease in the SFC was observed, but the decrease was at a level without any problems, and the SFC value was stabilized later. The details of the performance of the water absorbent resin (2) obtained are presented in Table 1. Meanwhile, even after a lapse of 365 days (12 months), there was neither a deterioration of physical properties nor a change in the particle size, and the apparatus operated stably.

Example 3

The same operation as that employed in Example 1 was carried out, except that the stretch tension (tension) of the metal sieve mesh of the classification step 3 used in Example 1 described above was changed to 45 [N/cm], and thus a water absorbent resin (3) was obtained.

While the water absorbent resin (3) obtained was continuously produced, sampling was carried out for every 1 ton, and a performance analysis was carried out for 20 tons of the water absorbent resin. The number of samples obtained was 20 samples, and the average CRC, AAP and SFC values were 30.3 [g/g] (CRC), 24.7 [g/g] (AAP), and $40[\times 10^{-7} \text{ cm}^3 \cdot \text{s} \cdot \text{g}^{-1}]$ (SFC), respectively. A slight decrease in the SFC was observed, but the decrease was at a level without any problems, and the SFC value was stabilized later. The details of the performance of the water absorbent resin (3) obtained are presented in Table 1. Meanwhile, even after a lapse of 365 days (12 months), there was neither a deterioration of physical properties nor a change in the particle size, and the apparatus operated stably.

Example 4

The same operation as that employed in Example 1 was carried out, except that the stretch tension (tension) of the metal sieve mesh of the classification step 3 used in Example 1 described above was changed to 85 [N/cm], and thus a water absorbent resin (4) was obtained.

While the water absorbent resin (4) obtained was continuously produced, sampling was carried out for every 1 ton, and a performance analysis was carried out for 20 tons of the water absorbent resin. The number of samples obtained was 20 samples, and the average CRC, AAP and SFC values were 30.3 [g/g] (CRC), 24.7 [g/g] (AAP), and $42[\times 10^{-7} \text{ cm}^3 \cdot \text{s} \cdot \text{g}^{-1}]$ (SFC), respectively. The details of the performance of the water absorbent resin (3) obtained are presented in Table 1. Meanwhile, since a deterioration of physical properties and a change in the particle size were confirmed after a stable operation of 180 days (6 months), the causes were investigated. Since it was discovered that the metal sieve mesh of the classification step 3 was partially destroyed, the metal sieve mesh was replaced.

Example 5

The same operation as that employed in Example 1 was carried out, except that the temperature and the stretch tension (tension) of the metal sieve of the classification step 3 used in Example 1 described above were changed to 30° C. and 50 [N/cm], respectively, and thus a water absorbent resin (5) was obtained.

While the water absorbent resin (5) obtained was continuously produced, sampling was carried out for every 1 ton, and a performance analysis was carried out for 20 tons of the water absorbent resin. The number of samples obtained was 20 samples, and the average CRC, AAP and SFC values were 30.2 [g/g] (CRC), 24.6 [g/g] (AAP), and $38[\times 10^{-7} \text{ cm}^3 \cdot \text{s} \cdot \text{g}^{-1}]$ (SFC), respectively. The details of the performance of the water absorbent resin (5) obtained are presented in Table 1. Meanwhile, although aggregates were observed in some of the water absorbent resin present on the metal sieve (⇒日文は "金属篩"), even after a lapse of 365 days (12 months), there was neither a deterioration of physical properties nor a change in the particle size, and the apparatus operated stably.

Comparative Example 1

The same operation as that employed in Example 1 was carried out, except that the stretch tension (tension) of all the metal sieve meshes of the classification steps 1 to 3 used in Example 1 described above was changed to 30 [N/cm], and thus a comparative water absorbent resin (1) was obtained.

While the comparative water absorbent resin (1) obtained was continuously produced, sampling was carried out for every 1 ton, and a performance analysis was carried out for 20 tons of the water absorbent resin. The number of samples obtained was 20 samples, and the average CRC, AAP and SFC values were 29.8 [g/g] (CRC), 23.9 [g/g] (AAP), and $34[\times 10^{-7} \text{ cm}^3 \cdot \text{s} \cdot \text{g}^{-1}]$ (SFC), respectively. The details of the performance of the comparative water absorbent resin (1) obtained are presented in Table 1. Meanwhile, since a deterioration of physical properties and a change in the particle size were confirmed after a stable operation of 60 days (2 months), the causes were investigated. Since it was discovered that some of the metal sieve meshes of the classification steps were destroyed, the metal sieve meshes were replaced.

Comparative Example 2

The same operation as that employed in Example 1 was carried out, except that the stretch tension (tension) of the metal sieve mesh of the classification step 3 used in Example 1 described above was changed to 30 [N/cm], and thus a comparative water absorbent resin (2) was obtained.

While the comparative water absorbent resin (2) obtained was continuously produced, sampling was carried out for every 1 ton, and a performance analysis was carried out for 20 tons of the water absorbent resin. The number of samples obtained was 20 samples, and the average CRC, AAP and SFC values were 29.8 [g/g] (CRC), 24.7 [g/g] (AAP), and $34[\times 10^{-7} \text{ cm}^3 \cdot \text{s} \cdot \text{g}^{-1}]$ (SFC), respectively. The details of the performance of the comparative water absorbent resin (2) obtained are presented in Table 1. Meanwhile, since a deterioration of physical properties and a change in the particle size were confirmed after a stable operation of 90 days (3 months), the causes were investigated. Since it was discovered that the metal sieve mesh of the classification step 3 was partially destroyed, the metal sieve mesh was replaced.

Comparative Example 3

The same operation as that employed in Example 1 was carried out, except that the stretch tension (tension) of the metal sieve mesh of the classification step 3 used in Example 1 described above was changed to 150 [N/cm], and thus a comparative water absorbent resin (3) was obtained.

While the comparative water absorbent resin (3) obtained was continuously produced, sampling was carried out for every 1 ton, and a performance analysis was carried out for 20 tons of the water absorbent resin. The number of samples obtained was 20 samples, and the average CRC, AAP and SFC values were 30.3 [g/g] (CRC), 24.7 [g/g] (AAP), and $42[\times 10^{-7} \text{ cm}^3 \cdot \text{s} \cdot \text{g}^{-1}]$ (SFC), respectively. The details of the performance of the comparative water absorbent resin (3) obtained are presented in Table 1. Meanwhile, since a deterioration of physical properties and a change in the particle size were confirmed after a stable operation of 60 days (2 months), the causes were investigated. Since it was discovered that the metal sieve mesh of the classification step 3 was partially destroyed, the metal sieve mesh was replaced.

Comparative Example 4

The same operation as that employed in Example 1 was carried out, except that the stretch tension (tension) of the metal sieve mesh of the classification step 1 used in Example 1 describe above was changed to 120 [N/cm], and thus a comparative water absorbent resin (4) was obtained.

While the comparative water absorbent resin (4) obtained was continuously produced, sampling was carried out for every 1 ton, and a performance analysis was carried out for 20 tons of the water absorbent resin. The number of samples obtained was 20 samples, and the average CRC, AAP and SFC values were 30.1 [g/g] (CRC), 24.5 [g/g] (AAP), and $41[\times 10^{-7} \text{ cm}^3 \cdot \text{s} \cdot \text{g}^{-1}]$ (SFC), respectively. The details of the performance of the comparative water absorbent resin (4) obtained are presented in Table 1. Meanwhile, since a deterioration of physical properties and a change in the particle size were confirmed after a stable operation of 60 days (2 months), the causes were investigated. Since it was discovered that some of the metal sieve mesh of the classification step 1 were destroyed, the metal sieve mesh was replaced.

Example 6

The same operation as that employed in Example 1 was carried out, except that an airbrush was installed below the metal sieve in the classification step 3 of Example 1 described above, and classification was carried out by using air having a dew point of −30° C., and thus a water absorbent resin (6) was obtained.

While the water absorbent resin (6) obtained was continuously produced, sampling was carried out for every 1 ton, and a performance analysis was carried out for 20 tons of the water absorbent resin. The number of samples obtained was 20 samples, and the average CRC, AAP and SFC values were 30.3 [g/g] (CRC), 24.7 [g/g] (AAP), and 46 [×10$^{-7}$ cm$^3$·s·g$^{-1}$] (SFC), respectively. The details of the performance of the water absorbent resin (6) obtained are presented in Table 1.

Example 7

The same operation as that employed in Example 1 was carried out, except that white (milky white) tapping balls having a diameter of 30 mm and a punching metal made of stainless steel (material: SUS304) having a hole diameter of 20 mm were installed below the metal sieve in the classification step 3 of Example 1 described above, and classification was carried out in the classification step 3 of Example 1 described above, and thus a water absorbent resin (7) was obtained.

While the water absorbent resin (7) obtained was continuously produced, sampling was carried out for every 1 ton, and a performance analysis was carried out for 20 tons of the water absorbent resin. The number of samples obtained was 20 samples, and the average CRC, AAP and SFC values were 30.4 [g/g] (CRC), 24.7 [g/g] (AAP), and 44 [×10$^{-7}$ cm$^3$·s·g$^{-1}$] (SFC), respectively. The details of the performance of the water absorbent resin (7) obtained are presented in Table 1.

Example 8

The same operation as that employed in Example 1 was carried out, except that classification was carried out after 1 wt % of calcium carbonate was added as a classification aid particle to the metal sieve in the classification step 3 of Example 1 described above, and a fine powder of the water absorbent resin and calcium carbonate were removed together, and thus a water absorbent resin (8) was obtained.

While the water absorbent resin (8) obtained was continuously produced, sampling was carried out for every 1 ton, and a performance analysis was carried out for 20 tons of the water absorbent resin. The number of samples obtained was 20 samples, and the average CRC, AAP and SFC values were 30.4 [g/g] (CRC), 24.1 [g/g] (AAP), and 45 [×10$^{-7}$ cm$^3$·s·g$^{-1}$] (SFC), respectively. The details of the performance of the water absorbent resin (8) obtained are presented in Table 1.

TABLE 1

| | Tension [N/cm] | | | Classification step 3 | Sieve replacement [days] | CRC [g/g] | AAP [g/g] | SFC [×10$^{-7}$ cm$^3$·s·g$^{-1}$] | Decrement of SFC [×10$^{-7}$ cm$^3$·s·g$^{-1}$] |
|---|---|---|---|---|---|---|---|---|---|
| | Classification 1 | Classification 2 | Classification 3 | | | | | | |
| Example 1 | 50 | 50 | 50 | — | 365 | 30.3 | 24.7 | 42 | 2 |
| Example 2 | 50 | 50 | 40 | — | 365 | 30.2 | 24.6 | 38 | 3 |
| Example 3 | 50 | 50 | 45 | — | 365 | 30.3 | 24.7 | 40 | 2 |
| Example 4 | 50 | 50 | 85 | — | 180 | 30.3 | 24.7 | 42 | 2 |
| Example 5 | 50 | 50 | 50 | — | 365 | 30.2 | 24.6 | 38 | 3 |
| Comparative Example 1 | 30 | 30 | 30 | — | 60 | 29.8 | 23.9 | 34 | 5 |
| Comparative Example 2 | 50 | 50 | 30 | — | 90 | 29.8 | 24.7 | 34 | 5 |
| Comparative Example 3 | 50 | 50 | 150 | — | 60 | 30.3 | 24.7 | 42 | 6 |
| Comparative Example 4 | 120 | 50 | 50 | — | 60 | 30.1 | 24.5 | 41 | 6 |
| Example 6 | 50 | 50 | 50 | O1) | | 30.3 | 24.7 | 46 | 1 |
| Example 7 | 50 | 50 | 50 | O2) | | 30.4 | 24.7 | 44 | 1 |
| Example 8 | 50 | 50 | 50 | O3) | | 30.3 | 24.1 | 45 | 1 |

1) Airbrush, 2) Tapping material, or 3) Calcium carbonate, was respectively used.

CONCLUSIONS

As indicated in Table 1, by controlling the tension (stretch tension) of the metal sieve meshes 35 to 100 [N/cm], and/or by using a tapping material, an airbrush and a classification aid, the various physical properties (SFC and the like) of the water absorbent resins obtainable are enhanced. Furthermore, by controlling the stretch tension (tension) of the metal sieve meshes to 35 to 100 [N/cm] in all the classification steps, the time period of continuous operation, that is, the time for replacement of metal sieve meshes, is increased. Further, it is shown that the stretch tension (tension) of the metal sieve meshes affects the physical property of a water absorbent resin, particularly the physical property obtained after surface crosslinking (particularly, liquid permeability); however, it is understood that when the stretch tension (tension) of the metal sieve meshes is controlled to 35 to 100 [N/cm], the metal sieve meshes stably operate for a long time period, and the stable operation contributes to stabilization of the physical property even at the time of continuous operation. Furthermore, generation or incorporation of aggregates can be reduced by increasing the temperature of the sieves. Patent Literature 1 to 30 described above neither discloses nor suggests the idea of the present invention.

INDUSTRIAL APPLICABILITY

A water absorbent resin which is free from coloration or foreign materials can be stably produced at low cost by continuous production in a huge scale (particularly 1 [t/hr] or more), and therefore the water absorbent resin of the present invention can be used in various sanitary materials including paper diapers and sanitary napkins, as well as in various applications of water absorbent resins.

In addition, the present patent application is based on Japanese Patent Application Nos. 2010-061223 and 2010-061224 filed Mar. 17, 2010, the entire disclosure of which is incorporated herein by reference.

The invention claimed is:

1. A method for producing a water absorbent resin comprising:
   a polymerization step of polymerizing an aqueous solution of acrylic acid (salt) to obtain a water-containing gel-like crosslinked polymer;
   a drying step of drying the water-containing gel-like crosslinked polymer to obtain a water absorbent resin powder;
   a classification step of classifying the water absorbent resin powder; and
   a surface crosslinking step of surface crosslinking the water absorbent resin powder,
   wherein in the classification step that is carried before the surface crosslinking step and/or after the surface crosslinking step, stretch tension (tension) of a metal sieve mesh used in the classification step is from 35 [N/cm] to 100 [N/cm],
   the method satisfying one or more of the following three requirements:
   (1) an airbrush is installed below the metal sieve mesh used in the classification step, in which the airbrush uses dry air having a dew point of 0° C. or lower, and the classifying apparatus is heated at 40° C. to 80° C.;
   (2) in the classification step, a classification aid particle having specific gravity larger than that of the water absorbent resin powder is added, and a fine powder of the water absorbent resin and the classification aid particle are removed, in which the classification aid particle is an inorganic fine particle or an organic fine particle; and
   (3) plural tapping balls or tapping blocks are installed below the metal sieve mesh used in the classification step, in which a gas stream passes through in the classification step, and the dew point of the gas stream is 15° C. or lower.

2. The method according to claim 1, wherein the material of the metal sieve mesh is SUS304 or SUS316, and the surface roughness (Rz) of the inner surface of the metal sieve mesh is 800 nm or less.

3. The method according to claim 1, wherein requirement (2) or (3) is satisfied and the metal sieve mesh is heated or kept warm to a temperature of 40° C. or higher.

4. The method according to claim 1, wherein requirement (2) is satisfied, a gas stream passes through in the classification step, and the dew point of the gas stream is 15° C. or lower.

5. The method according to claim 1, wherein in the classification step, removal of electricity is carried out by a ground connection with a ground resistance value of 100Ω or less.

6. The method according to claim 1, wherein the classification step is carried out under reduced pressure.

7. The method according to claim 1, wherein the damage to the metal sieve mesh is monitored by an acoustic emission (AE) method.

* * * * *